(12) United States Patent
Nejatollahi et al.

(10) Patent No.: US 10,905,771 B2
(45) Date of Patent: Feb. 2, 2021

(54) ANTI-MUC18 HUMAN IMMUNOTOXIN AND APPLICATIONS THEREOF

(71) Applicants: Foroogh Nejatollahi, Shiraz (IR); Mozafar Mohammadi, Shiraz (IR)

(72) Inventors: Foroogh Nejatollahi, Shiraz (IR); Mozafar Mohammadi, Shiraz (IR)

( * ) Notice: Subject to any disclaimer, the term of this patent is extended or adjusted under 35 U.S.C. 154(b) by 212 days.

(21) Appl. No.: 15/990,668

(22) Filed: May 27, 2018

(65) Prior Publication Data

US 2018/0271994 A1    Sep. 27, 2018

Related U.S. Application Data

(60) Provisional application No. 62/512,195, filed on May 30, 2017.

(51) Int. Cl.
```
A61K 47/68     (2017.01)
A61K 47/64     (2017.01)
A61K 39/395    (2006.01)
C07K 16/30     (2006.01)
```

(52) U.S. Cl.
CPC .... *A61K 47/6829* (2017.08); *A61K 39/39558* (2013.01); *A61K 47/6415* (2017.08); *A61K 47/6849* (2017.08); *A61K 47/6865* (2017.08); *A61K 47/6869* (2017.08); *C07K 16/3092* (2013.01); *C07K 2317/34* (2013.01); *C07K 2317/77* (2013.01)

(58) Field of Classification Search
None
See application file for complete search history.

(56) References Cited

U.S. PATENT DOCUMENTS

| | | |
|---|---|---|
| 6,924,360 B2 | 8/2005 | Green et al. |
| 7,067,131 B2 | 6/2006 | Gudas et al. |
| 9,782,500 B2 | 10/2017 | Bonsdorff et al. |

FOREIGN PATENT DOCUMENTS

EP    1382615 A1    1/2004

*Primary Examiner* — Sarvamangala Devi
(74) *Attorney, Agent, or Firm* — Bajwa IP Law Firm; Haris Zaheer Bajwa

(57) ABSTRACT

An anti-MUC18 immunotoxin including an anti-MUC18 single-chain variable fragment (scFv) with a nucleotide sequence as set forth in SEQ ID No. 3, and a truncated *Pseudomonas* exotoxin A (PEA) with a nucleotide sequence as set forth in SEQ ID No. 5. The truncated PEA may be conjugated with the scFv through a connector.

10 Claims, 19 Drawing Sheets
Specification includes a Sequence Listing.

FIG. 16

Translation of the V segment (MUC18-scFv L)

```
                              <--------------- FR 1 - IMGT --------------->
                    1            5              10           15            20            25
                    D  I  V  M  T  Q  S  P  S  S  L  S  A  S  I  G  D  R  V  T  I  T  C  R  A  S
MUC18_scFv_L        GAC ATC GTG ATG ACC CAG TCT CCA TCC TCC CTG TCT GCA TCT ATA GGG GAC AGA GTC ACC ATC ACT TGT CGG GCA AGT
                                Q                                                 V
humIGKV097 282 bp   --- --- CA- --- --- --- --- --- --- --A --- --- --- --- G-- --A --- --- --- --- --- --- --- --G ---

_____ CDR1 - IMGT _____           <--------------- FR 2 - IMGT
                            30                        35                        40           45            50
                    Q  G  I  S  N  F                       L  A  W  F  Q  Q  K  P  G  K  A  P  K  S
MUC18_scFv_L        CAG GGC ATT AGC AAT TTT ... ... ... ... ... ... TTA GCC TGG TTT CAG CAG AAA CCA GGG AAA GCC CCT AAG TCC
                                        Y
humIGKV097 282 bp   --- --- --- --- --- --A --- ... ... ... ... ... --- --- --- --- --- --- --- --- --- --- --- --- --- ---

--------->        _____ CDR2 - IMGT _____           <---------------
                              55                        60                        65           70            75
                    L  I  Y  A  A  S                       S  L  Q  S  G  V  P     S  R  F  S  G
MUC18_scFv_L        CTG ATC TAT GCT GCA TCC ... ... ... ... ... ... AGT TTG CAA AGT GGG GTC CCA ... TCA AGG TTC AGC GGC humIGKV097 282 bp   --- --- --- --- --- --- ... ... ... ... ... ... --- --- --- --- --- --- ... --- --- --- --- --- ---

-------- FR 3 - IMGT ------------------------------------>
                            80            85            90            95           100
                    S  G           S  G  T  D  F  T  L  A  I  S  S  L  Q  P  E  D  F  A  T  Y  Y  C
MUC18_scFv_L        AGT GGA ... ... TCT GGG ACA GAT TTC ACT CTC GCC ATC AGC AGC CTG CAG CCT GAA GAT TTT GCA ACT TAT TAC TGT
                                                                  T
humIGKV097 282 bp   --- --- ... ... --- --- --- --- --- --- --A --- --- --- --- --- --- --- --- --- --- --- --- --- --C _____ CDR3 - IMGT _____           <--------- FR4 - IMGT --------->
                        105           110  114                     120           125
                    L  Q  D  S  D  Y  P  L  T  F  G  G  G  T  K  L  E  I  K  R
MUC18_scFv_L        CTC CAA GAT TCC GAT TAT CCT CTC ACT TTC GGC GGA GGG ACC AAG CTG GAG ATC AAA CGT
                        Q     Y  N  S
humIGKV097 282 bp   --AA --G T-- AAT AG- --C
```

FIG. 17

ANTI-MUC18 HUMAN IMMUNOTOXIN AND APPLICATIONS THEREOF

CROSS-REFERENCE TO RELATED APPLICATION

This application claims the benefit of priority from U.S. Provisional Patent Application Ser. No. 62/512,195, filed on May 30, 2017, and entitled "RECOMBINANT IMMUNOTOXIN SCFV-PE TARGETING MUC18," which is incorporated herein by reference in its entirety.

TECHNICAL FIELD

The present disclosure generally relates to anti-tumor recombinant immunotoxins, particularly to an anti-MUC18 human immunotoxin, and more particularly to a method for killing cells overexpress MUC18 using an anti-MUC18 human immunotoxin.

BACKGROUND

Tumor associated antigens on the surface of malignant cells are effective targets for target-specific delivery of anti-cancer agents. MUC18 is a cell-surface glycoprotein associated with tumor progression and development of metastatic potential. The protein is overly expressed in different cancers such as melanoma cancer, prostate cancer, angiosarcoma, haemangioma, gestational trophoblastic tumors, leiomyosarcoma, Kaposi's sarcoma, schwannoma, some lung squamous and small cell carcinomas, some breast cancer, some neuroblastoma, and also cervical and endometrial cancer. Moreover, MUC18 is expressed on blood vessels and can promote tumor growth and angiogenesis. Therefore, MUC18 can be a promising target for a combined antitumor and anti-angiogenesis therapy.

Anti-MUC18 antibodies can inhibit angiogenesis, tumor growth, and suppress metastasis of melanoma. Single-chain variable fragment (scFv) is an antibody fragment including variable heavy (VH) and variable light (VL) chains which are linked by a polypeptide linker. The scFv may be used for diagnostic and therapeutic applications with improved pharmacokinetic properties. Human scFvs (HscFvs) selected by phage display technology have several advantages over antibodies selected by hybridoma technology. The advantages of human scFvs in clinical practice includes human origin that overcomes the problem of human anti-mouse antibody (HAMA) response induced by non-human monoclonal antibodies, high solid tumor penetration and high affinity.

These small human antibodies can be utilized for preparation of human recombinant immunotoxins. The human immunotoxins can be constructed by fusing HscFv to a toxin. Recombinant immunotoxins are developed to eliminate target cells that are resistant to standard chemotherapy. Human recombinant Immunotoxins are attractive candidates for cancer therapy because they combine the specificity of tumor-cell-reactive human antibodies with the high cytotoxic potency of naturally occurring toxins.

Regarding several advantages of human immunotoxin and expression of MUC18 in a number of cancer cells, there is a need for a high-affinity anti-MUC18 human scFv and a human recombinant immunotoxin against the MUC18 antigen. Moreover, there is a need for a cost-effective and efficient method for selectively killing cells which overexpress MUC18.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary anti-MUC18 human recombinant immunotoxin including an anti-MUC18 human single-chain variable fragment (anti-MUC18 HscFv) with a nucleotide sequence as set forth in SEQ ID No. 3 selected against an immunodominant epitope of MUC18 with an amino acid sequence as set forth in SEQ ID No. 25 and a truncated *Pseudomonas exotoxin* A (PEA) with a nucleotide sequence as set forth in SEQ ID No. 5.

The above general aspect may include one or more of the following features. In some exemplary implementations, the truncated PEA may be genetically fused to the anti-MUC18 HscFv through a connector with a nucleotide sequence as set forth in SEQ ID No. 7. In some exemplary embodiments, the anti-MUC18 human immunotoxin may have a nucleotide sequence as set forth in SEQ ID No. 1 and an amino acid sequence as set forth in SEQ ID No. 2.

According to some exemplary embodiments, the anti-MUC18 HscFv may have an amino acid sequence as set forth in SEQ ID No 4. In some exemplary embodiments, the immunodominant epitope of MUC18 may have an amino acid sequence as set forth in SEQ No 25. In some exemplary embodiments, the truncated PEA may include 259 residues from C-terminal of a mature PE. In some exemplary embodiments, the truncated PEA may have an amino acid sequence as set forth in SEQ ID No. 6

According to some exemplary embodiments, the truncated PEA may include a furin cleavage site with an amino acid sequence as set forth in SEQ ID No. 21, a domain Ib of PEA with an amino acid sequence as set forth in SEQ ID No. 22, a domain III of PEA with an amino acid sequence as set forth in SEQ ID No. 23, and a carboxyl-terminal region with an amino acid sequence as set forth in SEQ ID No. 24.

According to some exemplary embodiments, the anti-MUC18 HscFv may include a variable heavy (VH) chain with a nucleotide sequence as set forth in SEQ ID No. 9, and a variable light (VL) chain with a nucleotide sequence as set forth in SEQ ID No. 11. In some exemplary embodiments, the VH chain may be connected to the VL chain with a linker with an amino acid sequence as set forth in SEQ ID No. 14.

In another general aspect, the present disclosure describes an anti-MUC18 human antibody including a variable heavy chain (VH) with an amino acid sequence as set forth in SEQ ID No. 10, and a variable light chain (VL) with an amino acid sequence as set forth in SEQ ID No. 12. In some exemplary embodiments, the VH may be connected to the VL with a linker with an amino acid sequence as set forth in SEQ ID No. 14.

The above general aspect may include one or more of the following features. In some exemplary implementation, the anti-MUC18 human antibody may have a nucleotide sequence as set forth in SEQ ID No. 3 and an amino acid sequence as set forth in SEQ ID No. 4. In some exemplary embodiments, the anti-MUC18 human antibody may be a human single-chain variable fragment (anti-MUC18

HscFv). In some exemplary embodiments, the anti-MUC18 human antibody may be derived from human VH4 and VL1 gene families.

According to some exemplary implementations, the VH chain may include a complementarity-determining region 1 (CDR1) with an amino acid sequence as set forth in SEQ ID No. 15, a complementarity-determining region 2 (CDR2) with an amino acid sequence as set forth in SEQ ID No. 16, and a complementarity-determining region 3 (CDR3) with an amino acid sequence as set forth in SEQ ID No. 17.

According to some embodiments, the VL chain may include a CDR1 with an amino acid sequence as set forth in SEQ ID No. 18, a CDR2 with an amino acid sequence as set forth in SEQ ID No. 19, and a CDR3 with an amino acid sequence as set forth in SEQ ID No. 20.

In another general aspect, the present disclosure describes an exemplary method for killing MUC18-overexpressing cells. The method may include administering an anti-MUC18 human immunotoxin to the MUC18-overexpressing cells. The above general aspect may include one or more of the following features. In some exemplary embodiments, the anti-MUC18 human immunotoxin may include the anti-MUC18 HscFv with a nucleotide sequence as set forth in SEQ ID No. 3 and the truncated *Pseudomonas exotoxin A* (PEA) with a nucleotide sequence as set forth in SEQ ID No. 5. In some exemplary embodiments, the truncated PEA may be genetically fused to the anti-MUC18 HscFv through a connector.

According to some exemplary embodiments, the anti-MUC18 HscFv may include a variable heavy chain (VH) with an amino acid sequence as set forth in SEQ ID No. 10 and a variable light chain (VL) with an amino acid sequence as set forth in SEQ ID No. 12. In some exemplary embodiments, the VH may be connected to the VL with a linker.

According to some exemplary embodiments, the anti-MUC18 human immunotoxin may have a nucleotide sequence as set forth in SEQ ID No. 1 and an amino acid sequence as set forth in SEQ ID No. 2. In some exemplary embodiments, the linker may have a nucleotide sequence as set forth in SEQ ID No. 13 and an amino acid sequence as set forth in SEQ ID No. 14.

According to some exemplary embodiments, the connector may have a nucleotide sequence as set forth in SEQ ID No. 7 and an amino acid sequence as set forth in SEQ ID No. 8. In some exemplary embodiments, the MUC18-overexpressing cells may include one of prostate cancer cells and melanoma cancer cells.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 16 illustrate homology alignment of variable heavy (VH) chain of anti-MUC18 HscFv with an amino acid sequence (SEQ ID NO. 10) encoded by a nucleotide sequence (SEQ ID NO. 9), consistent with one or more exemplary embodiments of the present disclosure.

FIG. 17 illustrate homology alignment of variable light VL chain of anti-MUC18 HscFv with an amino acid sequence (SEQ ID NO. 12) encoded by a nucleotide sequence (SEQ ID NO. 11), consistent with one or more exemplary embodiments of the present disclosure.

DETAILED DESCRIPTION

Figure 1:
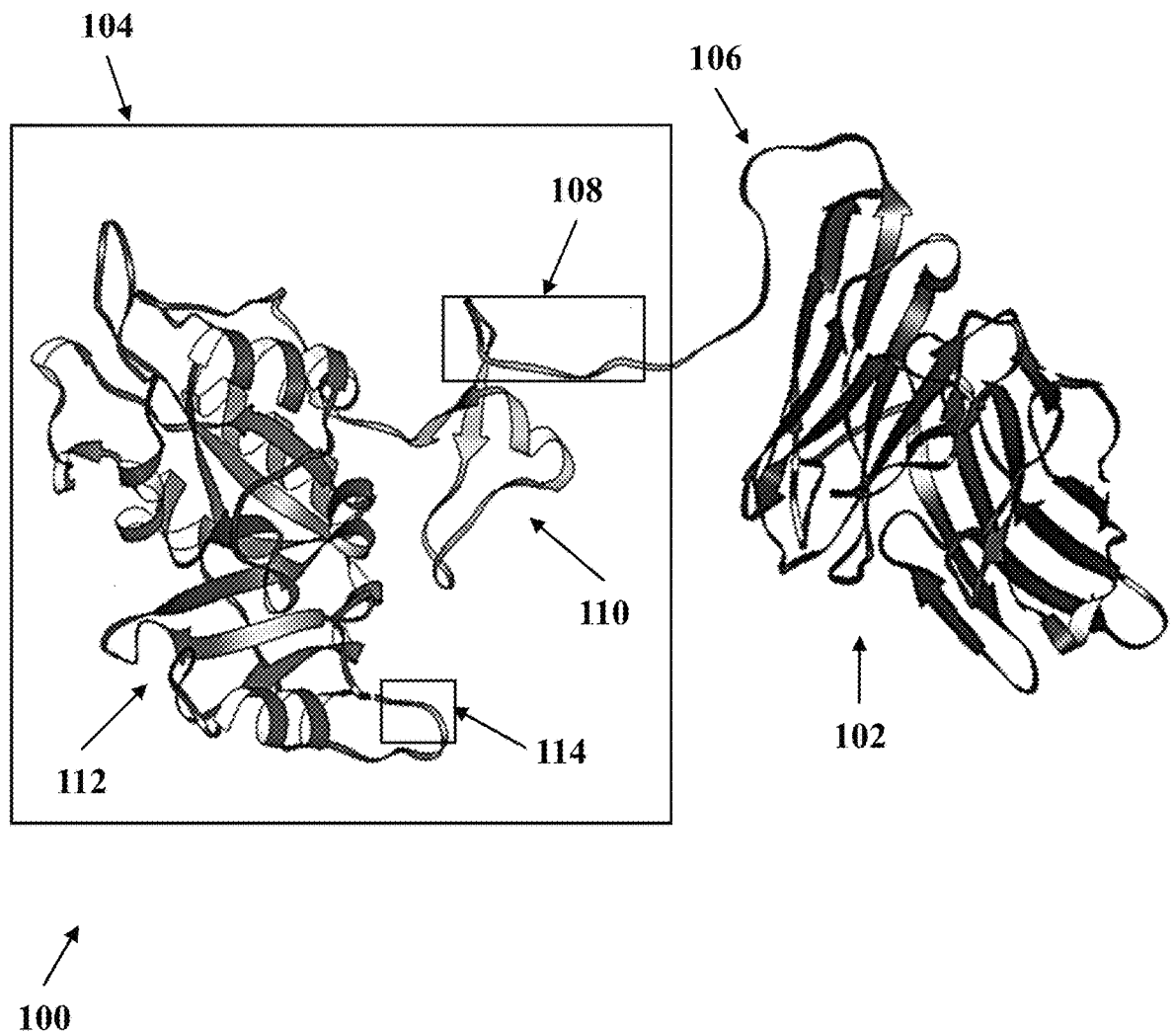
FIG. 1 illustrates an exemplary schematic for an anti-MUC18 human immunotoxin, consistent with one or more exemplary embodiments of the present disclosure.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Human immunotoxins are bifunctional molecules composed of human antibody covalently linked to a toxin that specifically bind to their target cells and kill them. Cytotoxicity effect of the human immunotoxins is dependent on the toxin in their structure. *Pseudomonas exotoxin* A (PEA) may be used as a toxin for human immunotoxin construction because it inhibits protein synthesis and leads to cell death. PEA may enter the target cells by inducing receptor-mediated endocytosis via a binding domain. Therefore, PEA may be a well-suited therapeutic for targeting and killing any cell such as a cancer cell by replacing the binding domain with a specific antibody or antibody fragment.

Disclosed herein is an exemplary anti-MUC18 human immunotoxin and its applications thereof for killing cells which overexpress MUC18 on their surfaces such as malignant cells in prostate cancer and melanoma cancer. The exemplary anti-MUC18 human immunotoxin may include a specific human single-chain variable fragment (HscFv) against an immunodominant epitope of the MUC18 antigen and a truncated *Pseudomonas exotoxin* A (PEA).

In some exemplary implementations, the anti-MUC18 human immunotoxin may be able to bind to the MUC18 antigens on the MUC18-overexpressing cell which may lead to rapid internalization of the anti-MUC18 human immunotoxin to the cells through endocytosis. Internalization of the anti-MUC18 human immunotoxin to the cells may induce apoptosis of the MUC18-overexpressing cells and kill them specifically through the function of the truncated PEA.

FIG. 1 illustrates an exemplary schematic for the anti-MUC18 human immunotoxin, consistent with one or more exemplary embodiments of the present disclosure. Referring to FIG. 1, anti-MUC18 human immunotoxin 100 may include anti-MUC18 HscFv 102 and truncated PEA 104. In an exemplary embodiment, anti-MUC18 HscFv 102 may be linked to truncated PEA 104 via connector 106. In some exemplary embodiments, truncated PEA 104 may include furin cleavage site 108, domain Ib of PEA 110, domain III of PEA 112, and carboxyl-terminal region 114.

In some exemplary embodiments, anti-MUC18 human immunotoxin 100 may have a nucleotide sequence as set forth in SEQ ID No. 1. In some exemplary embodiment, anti-MUC18 human immunotoxin 100 may have an amino acid sequence as set forth in SEQ ID No. 2.

In some exemplary embodiments, anti-MUC18 HscFv 102 may have a nucleotide sequence as set forth in SEQ ID No. 3, and an amino acid sequence as set forth in SEQ ID No. 4. In some exemplary embodiments, anti-MUC18 HscFv 102 may include a variable heavy (VH) chain and a variable light (VL) chain. In some exemplary embodiments, the VH chain may be connected to the VL chain with a linker with a nucleotide sequence as set forth in SEQ ID No. 13 and an amino acid sequence as set forth in SEQ ID No. 14.

In some exemplary embodiments, the VH chain may have a nucleotide sequence as set forth in SEQ ID No. 9 and an amino acid sequence as set forth in SEQ ID No. 10. In some exemplary embodiments, the VH chain may include three complementarity-determining regions (CDRs) including CDR1 with an amino acid sequence as set forth in SEQ ID No. 15, CDR2 with an amino acid sequence as set forth in SEQ ID No. 16, and CDR3 with an with an amino acid sequence as set forth in SEQ ID No. 17.

In some exemplary embodiments, the VL chain may have a nucleotide sequence as set forth in SEQ ID No. 11 and an amino acid sequence as set forth in SEQ ID No. 12. In some exemplary embodiments, the VL chain may include three complementarity-determining regions (CDRs) including CDR1 with an amino acid sequence as set forth in SEQ ID No. 18, CDR2 with an amino acid sequence as set forth in SEQ ID No. 19, and CDR3 with an with an amino acid sequence as set forth in SEQ ID No. 20.

In some exemplary embodiments, connector 106 may have a nucleotide sequence as set forth in SEQ ID No. 7 and an amino acid sequence as set forth in SEQ ID No. 8. In some exemplary embodiments, truncated PEA 104 may have a nucleotide sequence as set forth in SEQ ID No. 5 and an amino acid sequence as set forth in SEQ ID No. 6.

In some exemplary embodiments, truncated PEA 104 may include 259 residues from C-terminal of a mature PEA. In some exemplary embodiments, truncated PEA 104 may be prepared by removing all parts of domains I and II of PEA except furin cleavage site 108 but domain Ib 110 and domain III 112 which are necessary for toxicity may be kept. In some exemplary embodiments, carboxyl-terminal region 114 may be located at the end of truncated PEA 104 for increasing the cytotoxicity of anti-MUC18 human immunotoxin 100.

In some exemplary embodiments, furin cleavage site 108 may have an amino acid sequence as set forth in SEQ ID No. 21. In some exemplary embodiments, domain Ib of PEA 110 may have an amino acid sequence as set forth in SEQ ID No. 22. In some exemplary embodiments, domain III of PEA 112 may have an amino acid sequence as set forth in SEQ ID No. 23. In some exemplary embodiments, carboxyl-terminal region 114 may have an amino acid sequence as set forth in SEQ ID No. 24.

In some exemplary implementations, the anti-MUC18 human immunotoxin may be used for specifically killing cells which overexpress MUC18 on their surfaces by administering the anti-MUC18 human immunotoxin to MUC18-overexpressing cells. In some exemplary embodiments, the MUC18-overexpressing cells may include one of prostate cancer cells and melanoma cancer cells. In some exemplary embodiments, the anti-MUC18 human immunotoxin may have a half maximal inhibitory concentration (IC50) between about 2 nM and about 7 nM.

In some exemplary implementations, after administering the anti-MUC18 human immunotoxin to MUC18-overexpressing cells, the anti-MUC18 human immunotoxin may specifically bind to the MUC18 antigens on the MUC18-overexpressing cell using the anti-MUC18 HscFv in its structure. In some exemplary embodiments, after binding the anti-MUC18 human immunotoxin to the MUC18-overexpressing cells, the anti-MUC18 human immunotoxin may be internalized into the MUC18-overexpressing cells through endocytosis which may induce apoptosis inside the MUC18-overexpressing cells and kill them.

EXAMPLES

Example 1: Generation of an Anti-MUC18 HSCFV Using Phage Display Method

An anti-MUC18 HscFv was generated using phage display method according to following steps of producing HscFv-displaying phages using a human scFv library, forming bound phages by adding the HscFv-displaying phages to MUC18 immunodominant epitope, selecting the specific and high-affinity phages from the bound phages by enriching the bound phages, identifying an anti-MUC18 HscFv by sequencing anti-MUC18 HscFv of the specific high-affinity phages.

HscFv-phage antibodies were produced by rescuing HscFv phages from a human scFv library. The phage transformed E. coli cells of the human scFv library containing phagemids (pCANTAB5 vectors) encoding HscFv genes were grown overnight on 2TYG Agar/ampicillin medium at a temperature of about 30° C. in a plate.

In order to rescue the phages of the HscFv library, a helper phage was incubated with the phage transformed E coli to provide structural proteins for phage packaging. All transformed bacteria were scraped in a 50 ml 2TY broth medium and incubated at 37° C. for about 1 hr. After reaching the optical density (OD) to 1, M13KO7 helper phage was added to the 2TY broth medium containing the transformed bacteria and mixed. The flask containing the grown transformed bacteria was incubated at a temperature of about 37° C. for a time period of 30 minutes followed by shaking at a temperature of about 37° C. for a time period of about 30 min.

The bacterial suspension containing phage-infected bacteria was transferred to a 50 ml tube and centrifuged at 3500 RPM for a time period of about 20 minutes. The supernatant was poured out and the bacterial pellet was transferred to 50 ml 2TY broth medium containing Ampicillin with a concentration of about 100 µg/ml and kanamycin with a concentration of about 50 µgml$^{-1}$ without glucose and cultured overnight with shaking at a temperature of about 30° C. At the end, the culture was centrifuged at 5500 RPM for 20 min. and the supernatant containing phage antibody was filtered and stored at 4° C.

In the next step, bound phages were formed by adding the HscFv-displaying phages to an immunodominant epitope of the MUC18 antigen. The immunodominant epitope of the MUC18 antigen was identified and selected using bioinformatics methods as follows. Primary structure of the MUC18 antigen including cytoplasmic and extracellular regions and also glycosylated regions was studied using web server of UniProt. Also, UniProt server was used to retrieve the amino acid sequence of the MUC18 antigen.

According to Uniprot information, amino acids from 1 to 23 of the MUC18 antigen may be specified as a signal sequence and amino acids from 24 to 646 of the MUC18 antigen may be related to the main chain of cell surface glycoprotein MUC18. Moreover, amino acids from 24 to 559 may correspond to the extracellular region, from 560 to 583 may correspond to the helical region, and from 584 to 646 may correspond to the cytoplasmic region of the MUC18 antigen. After using the Uniprot, antigenic regions of the MUC18 antigen were identified by applying the amino acid sequence of the extracellular region of the MUC18 antigen to EpiC web server.

Three-dimensional structure of the extracellular domain of MUC18 molecule was simulated by Phyre2 server which employs a comparative modeling algorithm. Afterward, the tertiary structure of modeled receptor was evaluated by the Chimera program. Among identified immunodominant epitopes of the MUC18 antigen by EpiC web server, a 10-amino acid region was selected according to criterions such as being exposed, non-glycosylation, and distance of those amino acids from the cytoplasmic membrane. Also, in order to avoid cross-reaction phenomenon, the selected immunodominant epitope of the MUC18 antigen was blasted using NCBI server to avoid cross reaction phenomenon. The immunodominant epitope of the MUC18 antigen as set forth in SEQ ID No. 25 was amino acids from 471 to 480 residues from C terminal of the MUC18 antigen.

After selecting the immunodominant epitope of the MUC18 antigen, in order to select the specific HscFvs against MUC18, the immunodominant epitope of the MUC18 antigen with a concentration of about 100 µg/ml in phosphate-buffered saline (PBS) was coated on an immunotube overnight at a temperature of about 4° C. Afterward, the tube was washed four times with PBS and blocked with skimmed milk with a concentration of about 2% weight/volume at a temperature of about 37° C. for a time period of about 2 hours. The immunotube coated with the immunodominant epitope of the MUC18 antigen was washed six times with TWEEN 20 with a concentration of about 0.05% weight-volume and six times with PBS to remove the extra amount of the immunodominant epitope of the MUC18 antigen.

Bound phages were formed by incubating a solution of the HscFv-displaying phages to the coated immunotube for a time period of about 2 hours at room temperature. The solution of the HscFv-displaying phages was formed by diluting the HscFv-displaying phages with a concentration of about 10$^9$ CFU/ml with an equal volume of a 2% skimmed milk as a blocking solution. The coated immunotube containing HscFv-displaying phages was washed several times to remove unbound and non-specific HscFv-displaying phages. Following washing, the bound phages were eluted from the coated immunotube with log-phase TG1 E. coli cells using an incubation temperature 37° C. for a time period of about 1 hour.

In the next step, high-affinity HscFv-displaying phage which specifically binds to the immunodominant epitope of the MUC18 antigen was selected from the bound phages by enriching the bound phages using three rounds of panning the bound phages against the immunodominant epitope of the MUC18 antigen. Panning the bound phages against the immunodominant epitope of the MUC18 antigen was done by incubating the bound phages of previous round of panning with the immunodominant epitope of the MUC18 coated on the immunotube, and eluting the bound phages of the present panning round from the tube.

In each round of panning, bound phages were enriched and bound phages with higher affinity were selected for the next round. In the final round of panning, a HscFv-displaying phage with the highest affinity for the immunodominant epitope of the MUC18 antigen was selected as a specific anti-MUC18 HscFv-displaying phage. In the next step, the anti-MUC18 HscFv was characterized using PCR, DNA fingerprinting analysis, and sequencing anti-MUC18 HscFv of the selected anti-MUC18 HscFv-displaying phage.

Before and after four rounds of panning, colony polymerase chain reaction (colony PCR) of randomly selected library clones were done using vector primers to amplify the HscFvs and verify the presence of an expected band with a molecular size of about 950 base pair (bp) corresponding to the HscFv sequence within the phagemid vector. Prior to conducting PCR on the HscFv library clones, transformed E coli cells were grown on 2TYG medium containing ampicillin at a temperature of about 30° C. overnight and about 20 different single colonies were picked off and incubated at a temperature of about 94° C. for a time period of about 10 minutes to lyse bacterial cells and prepare the DNA template for PCR.

Figure 2:
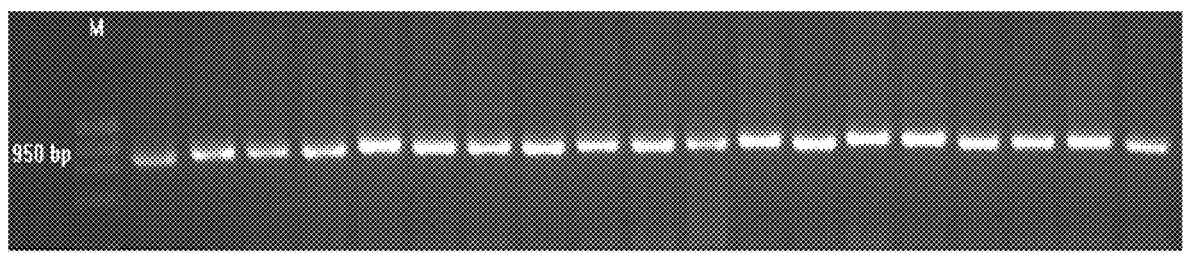
FIG. 2 illustrates results of gel electrophoresis profile of polymerase chain reaction (PCR) of HscFv library colonies before any rounds of panning using vector primers, consistent with one or more exemplary embodiments of the present disclosure.

After conducting PCR on the HscFv library, agarose gel electrophoresis was done to analyze the PCR products and check their size. FIG. 2 shows results of gel electrophoresis profile of polymerase chain reaction (PCR) of the HscFv library colonies before any rounds of panning using vector primers, consistent with one or more exemplary embodiments of the present disclosure. Referring to FIG. 2, the expected band corresponding to the HscFv sequence with a molecular size of about 950 bp using vector primers was observed. Therefore, it verifies the presence of the HscFvs in the HscFv library colonies.

Moreover, DNA fingerprinting analysis was carried out on PCR products of 20 colonies of the HscFv library clones and anti-MUC18 HscFv clones after four round of panning. The PCR products of 20 colonies of the HscFv library with an amount of about 17 μl was digested with a mixture of about 1 μl of MvaI restriction endonuclease and about 2 μl buffer at a temperature of about 37° C. for a time period of about 2 hours and run on a agarose gel with a concentration of about 3%.

Figure 3:
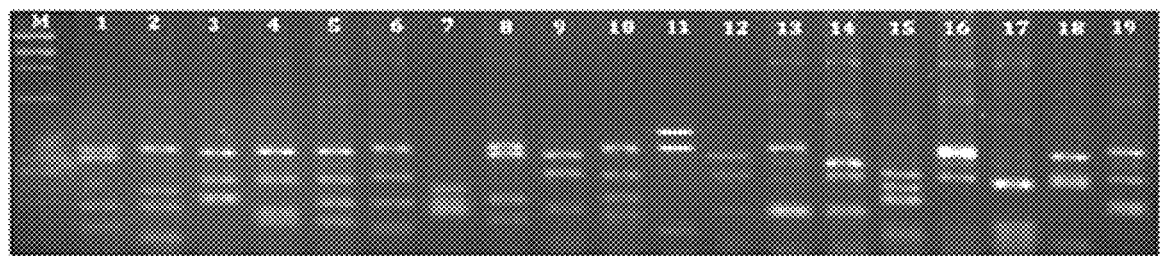
FIG. 3 illustrates DNA fingerprinting patterns of HscFv library clones before any rounds of panning, consistent with one or more exemplary embodiments of the present disclosure.

FIG. 3 shows DNA fingerprinting patterns of HscFv library clones before any rounds of panning, consistent with one or more exemplary embodiments of the present disclosure. Referring to FIG. 3, fingerprinting patterns demonstrate that the HscFv library colonies carried different HscFv sequences since their digestion patterns were different among each colony. Therefore, the library was diverse and heterogeneous.

Figure 4:
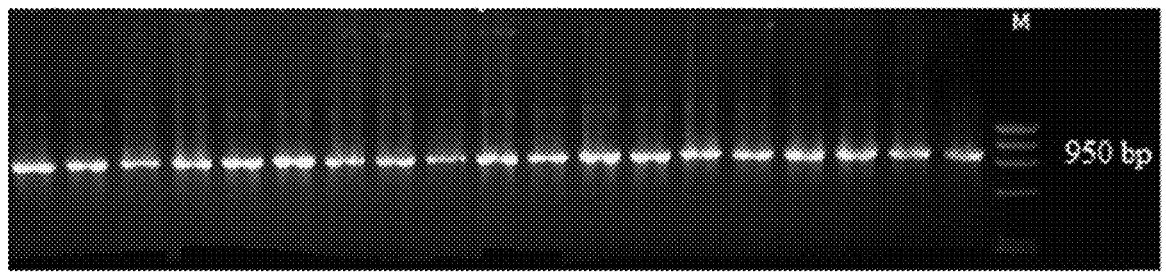
FIG. 4 illustrates results of gel electrophoresis profile of polymerase chain reaction (PCR) of the colonies containing anti-MUC18 HscFv-displaying phage using vector primers after four round of panning, consistent with one or more exemplary embodiments of the present disclosure.

After conducting PCR on the anti-MUC18 HscFv clones after four round of panning, agarose gel electrophoresis was done to analyze the PCR products and check their size. FIG. 4 shows results of gel electrophoresis profile of polymerase chain reaction (PCR) of the colonies containing anti-MUC18 HscFv-clones after four round of panning using vector primers, consistent with one or more exemplary embodiments of the present disclosure. Referring to FIG. 4, the expected band corresponding to the anti-MUC18 HscFv sequence with a molecular size of about 950 bp using vector primers was observed. Therefore, it confirmed the presence of the HscFv in the PCR products of the colonies containing anti-MUC18 HscFv after four round of panning.

Figure 5:
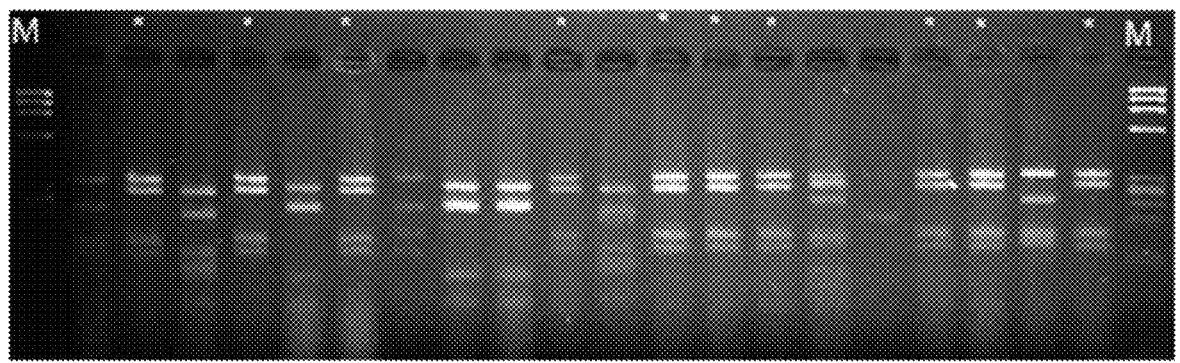
FIG. 5 illustrates DNA fingerprinting patterns of the colonies containing anti-MUC18 HscFv-displaying phage after four round of panning, consistent with one or more exemplary embodiments of the present disclosure.

DNA fingerprinting analysis was done on the colonies containing anti-MUC18 HscFvs after four round of panning. FIG. 5 shows DNA fingerprinting patterns of the colonies containing anti-MUC18 HscFv clones after four round of panning, consistent with one or more exemplary of the present disclosure. Referring to FIG. 5, one dominant pattern was obtained with a frequency of 50% in 10 colonies out of 20 colonies panned against the immunodominant epitope of the MUC18 antigen. Domination of a particular pattern of the PCR products against the immunodominant epitope of the MUC18 antigen indicates enrichment of the high-affinity HscFv-displaying phages against the immunodominant epitope of the MUC18 antigen. One colony from the dominant digestion pattern was employed for further characterization as a colony containing anti-MUC18 HscFv.

DNA sequencing of the selected clone containing the anti-MUC18 HscFv was done on an extracted plasmid containing the anti-MUC18 HscFv using pCANTAB5 vector specific primers. After sequencing the anti-MUC18 HscFv, the final sequence was found by creating DNA contig using Vector NTI 10 software. The DNA sequence of the anti-MUC18 HscFv was set forth in SEQ ID No. 3.

Figure 16:
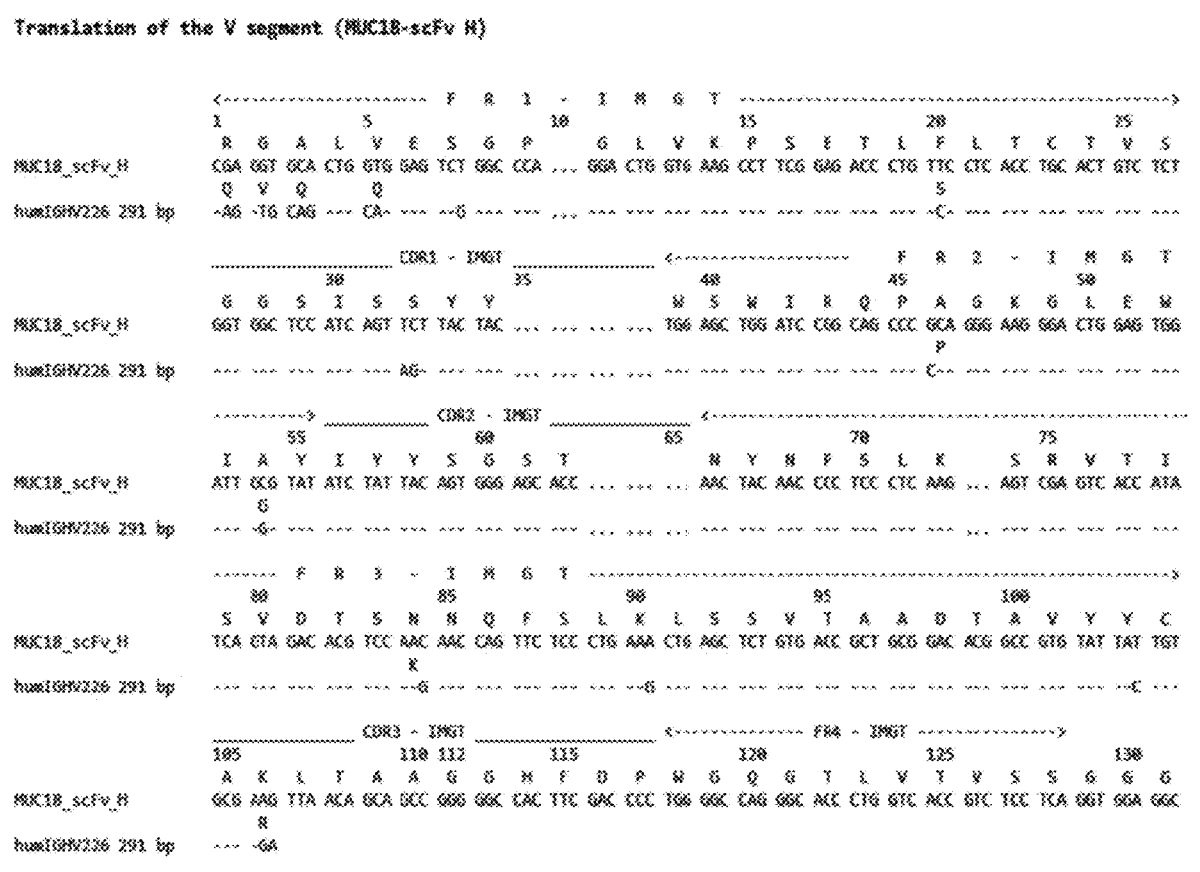

Moreover, homology alignment of the selected anti-MUC18 HscFv was done. Homology alignment using VBASE2 ID showed that the heavy chain variable region of the selected anti-MUC18 HscFv was derived from the human VH4 gene family. FIG. 16 shows homology alignment of VH region of anti-MUC18 HscFv, consistent with one or more exemplary embodiments of the present disclosure. Referring to FIG. 16, 79% similarities with human germ-line IGHV4-59*09 (humIGHV226) allele was observed. The light chain variable region of the scFv was derived from the kappa chain human VL1 gene family. FIG. 17 shows homology alignment of VL region of anti-MUC18 HscFv, consistent with one or more exemplary embodiments of the present disclosure. Referring to FIG. 17, 84% similarities with human germ-line IGKV1-16*01 (humIGHV097) allele were observed.

Several amino acid residues in CDR regions of anti-MUC18 HscFv were changed in comparison with germ-line sequences which confirmed the specificity changes of the anti-MUC18 HscFv. Referring again to FIG. 16, amino acid changes included arginine (R) in place of lysine (K) in the CDR3 of VH sequence. Referring again to FIG. 17, amino acid changes in the VL region included tyrosine (Y) in place of phenylalanine (F) in CDR1, glutamine (Q) in place of leucine (L), tyrosine (Y) in place of aspartic acid (D), asparagine (N) in place of serine (S), and serine (S) in place of aspartic acid in CDR3 of VL sequence of the anti MUC18 HscFv.

Example 2: Determining Specificity of the Anti-MUC18 HSCFV to the Immunodominant Epitope of the MUC18 Antigen Specificity of the anti-MUC18 HscFv-displaying phages to the immunodominant epitope of the MUC18 antigen was determined using enzyme-linked immunosorbent assay (ELISA). A 96 well polystyrene ELISA plate was coated with 100 μg/ml of the immunodominant epitope of the MUC18 antigen. The wells were blocked with 2% skimmed milk and incubated at 37° C. for a time period of 2 hr. After washing three times with PBS/TWEEN 20 and three times with PBS, anti-MUC18 phage antibodies were added to each well and incubated at room temperature for a time period of 2 hr. Following washing, the plate was incubated with rabbit anti-Fd bacteriophage antibody for a time period of about 1 hr. Finally, the plate was washed and incubated with HRP conjugated anti-rabbit IgG for a time period of 1 hr at a temperature of about 37° C. Afterward, substrate (TMB) and $H_2SO_4$ as stop solution were added.

Figure 6:
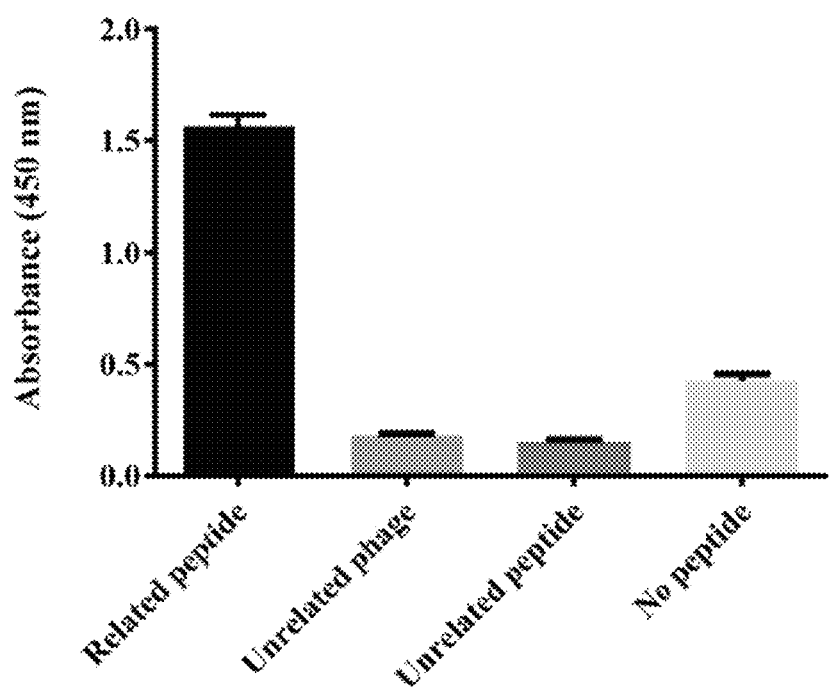
FIG. 6 illustrates absorbance of the anti-MUC18 HscFv against related and unrelated epitopes, consistent with one or more exemplary embodiments of the present disclosure.

In order to evaluate the result of ELISA method, optical density (OD) of bound phage in each well was read at a wavelength of about 450 nm using an ELISA reader, and the average absorbance of the bound phage in each well was calculated. Also, wells containing an unrelated peptide, an unrelated phage, and no peptide were considered as control groups. FIG. 6 shows absorbance of the bound phages against related and unrelated epitopes, consistent with one or more exemplary embodiments of the present disclosure.

Referring to FIG. 6, the mean absorbance of the bound anti-MUC18 HscFv-displaying phages in the well containing the immunodominant epitope of the MUC18 antigen was about 1.6 while the mean absorbance of the bound anti-MUC18 HscFv-displaying phages in the well containing an unrelated peptide was about 0.1 and in the well containing no peptide was about 0.42. In addition, the mean absorbance of the bound unrelated phage to the immunodominant epitope of the MUC18 antigen was about 0.17.

Referring again to FIG. 6, the weakest bindings were observed in the well with no coated peptide with OD of about 0.4. Moreover, the strongest bindings were detected in the well containing the anti-MUC18 HscFv bound to the immunodominant epitope of the MUC18 antigen with an OD 4 times greater than OD of peptide well as a negative control. Therefore, it indicates the significant affinity of the anti-MUC18 HscFv-displaying phages to the immunodominant epitope of the MUC18 antigen. Also, result of the ELISA assay demonstrates that the panning procedure for identifying the anti-MUC18 HscFv-displaying phage has been successfully performed and the isolated clone containing anti-MUC18 HscFv-displaying phage specifically react with the immunodominant epitope of the MUC18 antigen.

Example 3: Phage Internalization of the Anti-MUC18 HSCFV

In this example, internalization of the anti-MUC18 HscFv-displaying phages was investigated as follows. Human prostate cancer (DU145) and melanoma (A375) cell lines as MUC18-overexpressing cell lines were cultured in RPMI-1640 medium as test groups. Also, Breast cancer (SKBR3) cell line was cultured in RPMI-1640 medium as a negative group. All media were supplemented with 10% Fetal Bovine Serum (FBS), 100 U/ml penicillin, and 100 mg/ml streptomycin and they were kept in a humidified $CO_2$ incubator at a temperature of about 37° C. In all experiments, cells were detached with about 0.25% trypsin and about 0.02% EDTA.

In order to assess the internalization property of the anti-MUC18 HscFv-displaying phages, about $5 \times 10^5$ subconfluent adherent cells were incubated with about $10^{12}$ colony forming units (CFU) of phages for a time period of about 2 hours. This step was performed at a temperature of about 4° C. to allow phage binding without internalization. Subsequently, the cells were washed extensively with phosphate-buffered saline (PBS) to remove non-specifically or weakly bound phages.

Afterward, the cells were incubated with the bound anti-MUC18 HscFv-displaying phages at a temperature of about 37° C. for a time period of about 30 minutes to allow endocytosis of the bound anti-MUC18 HscFv-displaying phages. The cells were stripped three times with a low-pH glycine buffer to remove bound anti-MUC18 HscFv-displaying phages to the cell surface, trypsinized and washed with PBS to remove anti-MUC18 HscFv-displaying phages which were bound to the extracellular matrix or to the culture plate. Finally, the cells were lysed with high-pH triethylamine (TEA).

The cell lysate containing anti-MUC18 HscFv-displaying phages were recovered and used to infect E. coli TG1 cells for titration of the internalized anti-MUC18 HscFv-displaying phages and determining the number of anti-MUC18 HscFv-displaying phage per cell. As a result of titration, it was found that 30 anti-MUC18 HscFv-displaying phages were internalized per A375 cell. On the other hand, it was found that only 6 anti-MUC18 HscFv-displaying phages per SKBR3 cell as a negative control were internalized.

Example 4: Production of an Anti-MUC18 Human Immunotoxin

In this example, an exemplary anti-MUC18 human immunotoxin including an anti-MUC18 HscFv and a truncated PEA toxin was produced using the following steps: optimizing codons of the truncated PEA, forming the recombinant anti-MUC18 immunotoxin by fusing the nucleotide sequence of the anti-MUC18 HscFv and the truncated PEA, sequencing the human recombinant immunotoxin, expressing producing the anti-MUC18 human immunotoxin by transforming expression host cells with the recombinant vector containing the anti-MUC18 human immunotoxin.

In order to optimize the codon of the truncated PEA, Optimum Gene algorithm was used to optimize a variety of parameters that are critical to the expression efficiency of the anti-MUC18 human immunotoxin, including codon adaptation index (CAI), GC content, and ribosomal binding sites (RBSs). After codon optimization, the CAI index of the truncated PEA was about 0.90 which is more than 0.8 as an acceptable index. Also, the optimized codons have been distributed along the length of the gene sequence.

Moreover, the average GC content of the optimized truncated PEA was about 61.84% while the GC content of the original truncated PEA was about 73.42%. The ideal GC content of a sequence is between 30% and 70%. In order to optimize the RBSs of the truncated PEA, the original RBSs of the truncated PEA were omitted after optimization because of the presence of a RBS in the pET-28a (+) expression vector. Furthermore, the sequence of the truncated PEA was checked for restriction endonucleases sites, and restriction endonucleases sites of NheI and NcoI enzymes were selected for use in the cloning process.

In the next step, the recombinant vector containing the anti-MUC18 human immunotoxin was formed by fusing the nucleotide sequence of the anti-MUC18 HscFv and the truncated PEA. At first, the anti-MUC18 HscFv was amplified by a polymerase chain reaction (PCR) using gene cloning primers. Moreover, NcoI and NheI restriction sites, which are located in multiple-cloning sites of pET28a(+) vector were included to 5' end of forward cloning primer and 3' end of reverse cloning primers.

Moreover, while Pfu DNA polymerase has a proof reading property, the PCR of the anti-MUC18 HscFv was done using Pfu enzyme to obtain adequate amounts of the nucleotide sequence of the anti-MUC18 HscFv as a DNA template. Optimized PCR condition for amplifying the nucleotide sequence of the anti-MUC18 HscFv includes denaturation, annealing, and extension steps.

The denaturation step was done at a temperature of about 94° C. for a time period of about 1 min. The cloning primers were annealed to the single-stranded DNA templates in the annealing step at a temperature of about 69° C. for a time period of about 1 min. At the end, new nucleotide sequences of anti-MUC18 HscFv were generated in the extension step at a temperature of about 72° C. for a time period of about 2 min.

Figure 7:
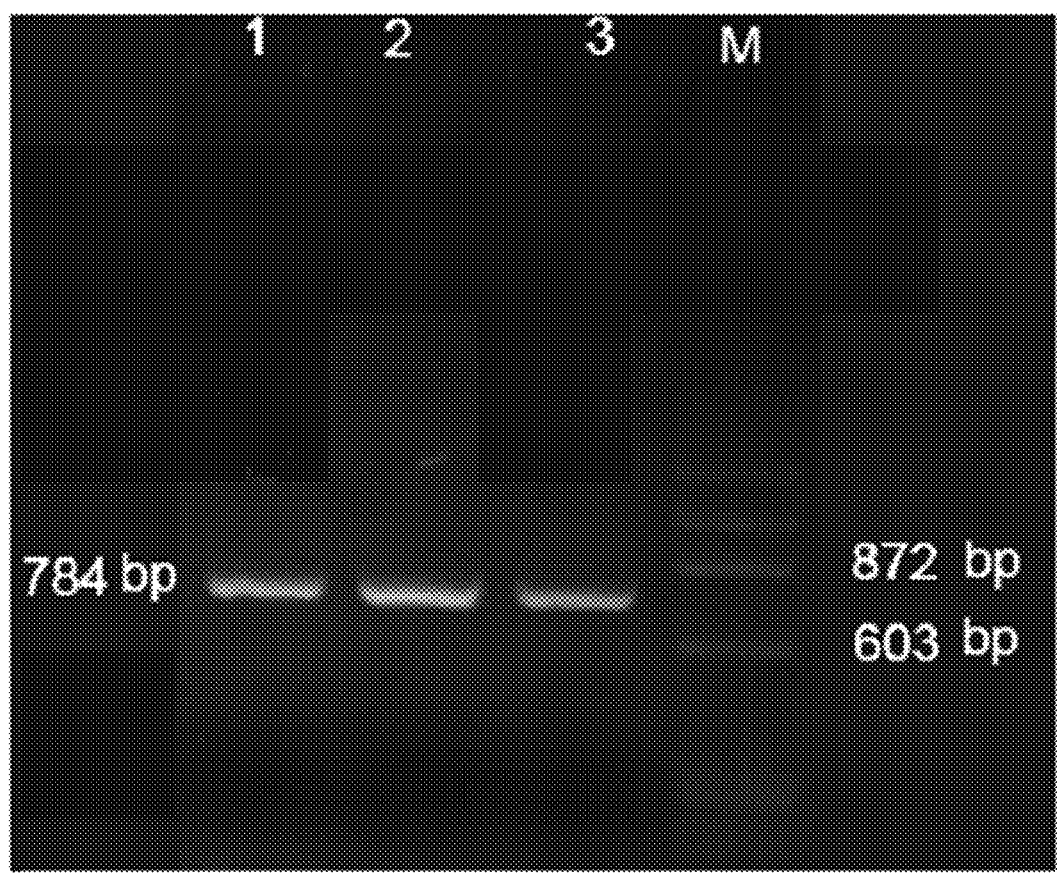
FIG. 7 illustrates a DNA band on an agarose gel corresponding to the amplified nucleotide sequence of the anti-MUC18 HscFv using cloning primers, consistent with one or more exemplary embodiments of the present disclosure.

FIG. 7 shows a DNA band on an agarose gel corresponding to the amplified nucleotide sequence of the anti-MUC18 HscFv using cloning primers, consistent with one or more exemplary embodiments of the present disclosure. The DNA marker was øX174 DNA marker. Referring to FIG. 7, the amplified anti-MUC18 HscFv has a molecular size of about 784 base pair (bp). Afterward, the amplified nucleotide sequences of the anti-MUC18 HscFv and the pET-28a (+) cloning vector were double digested by NcoI and NheI restriction endonucleases using a standard protocol.

Figure 8A:
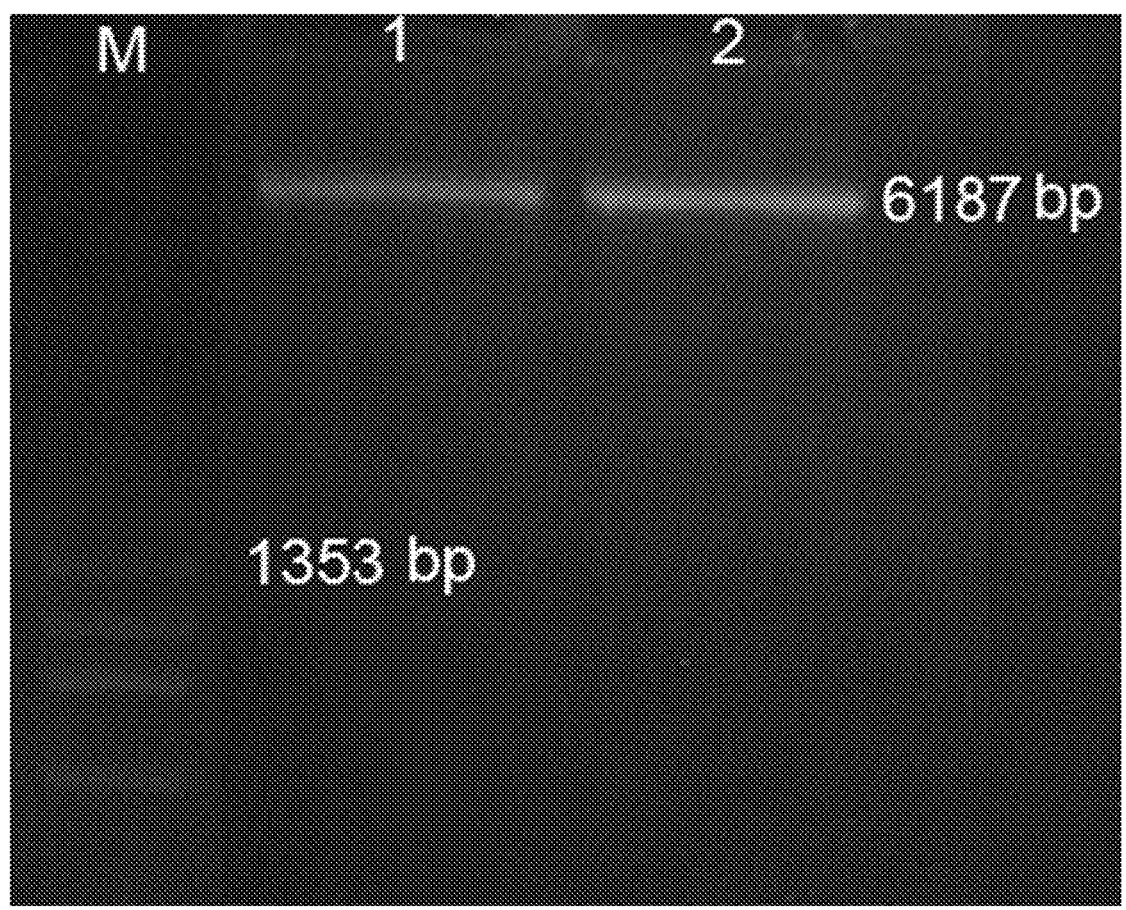
FIG. 8A illustrates a gel agarose electrophoresis of the double digested pET-28a (+) cloning vector (Lanes 1 and 2), consistent with one or more exemplary embodiments of the present disclosure.

FIG. 8A illustrates a gel agarose electrophoresis of the double digested pET-28a (+) cloning vector (Lanes 1 and 2), consistent with one or more exemplary embodiments of the present disclosure. Referring to FIG. 8A, the double digested pET-28a (+) cloning vector shows one DNA band with a molecular size of about 6187 bp. The double digested pET-28a (+) cloning vector was purified by a gel extraction method using a standard protocol.

In the next step, the nucleotide sequence of the anti-MUC18 HscFv was ligated to the purified double digested pET-28a (+) cloning vector containing nucleotide sequence related to the truncated PEA toxin using a standard protocol with a ratio of vector:nucleotide sequence of the anti-MUC18 HscFv of about 1:3. Ligation of the anti-MUC18 HscFv into the pET-28a (+) cloning vector produced a single clone including an insert with a molecular size of about 1530 bp, which is an expected size of the nucleotide sequence of the anti-MUC18 human immunotoxin.

After ligation, the anti-MUC18 human immunotoxin as a fusion protein cloned into the pET-28a (+) cloning vector, was sequenced. Sequencing the anti-MUC18 human immunotoxin was done in both the forward and reverse directions using T7 universal primers. As a result of the sequencing analysis, the anti-MUC18 human immunotoxin has a nucleotide sequence as set forth in SEQ ID No. 1 and an amino acid sequence as set forth in SEQ ID No. 2.

In the next step, the ligation product, which was the recombinant pET-28a (+) cloning vector including the nucleotide sequence of the anti-MUC18 human immunotoxin, was used to transform competent DH5α *E. coli* bacteria as a cloning host using a standard protocol. After transformation, PCR screening of the transformed DH5α *E. coli* clones using T7 sequencing universal primers was done to identify positive clones containing the recombinant pET-28a (+) cloning vector including the nucleotide sequence of the anti-MUC18 human immunotoxin.

Figure 8B:
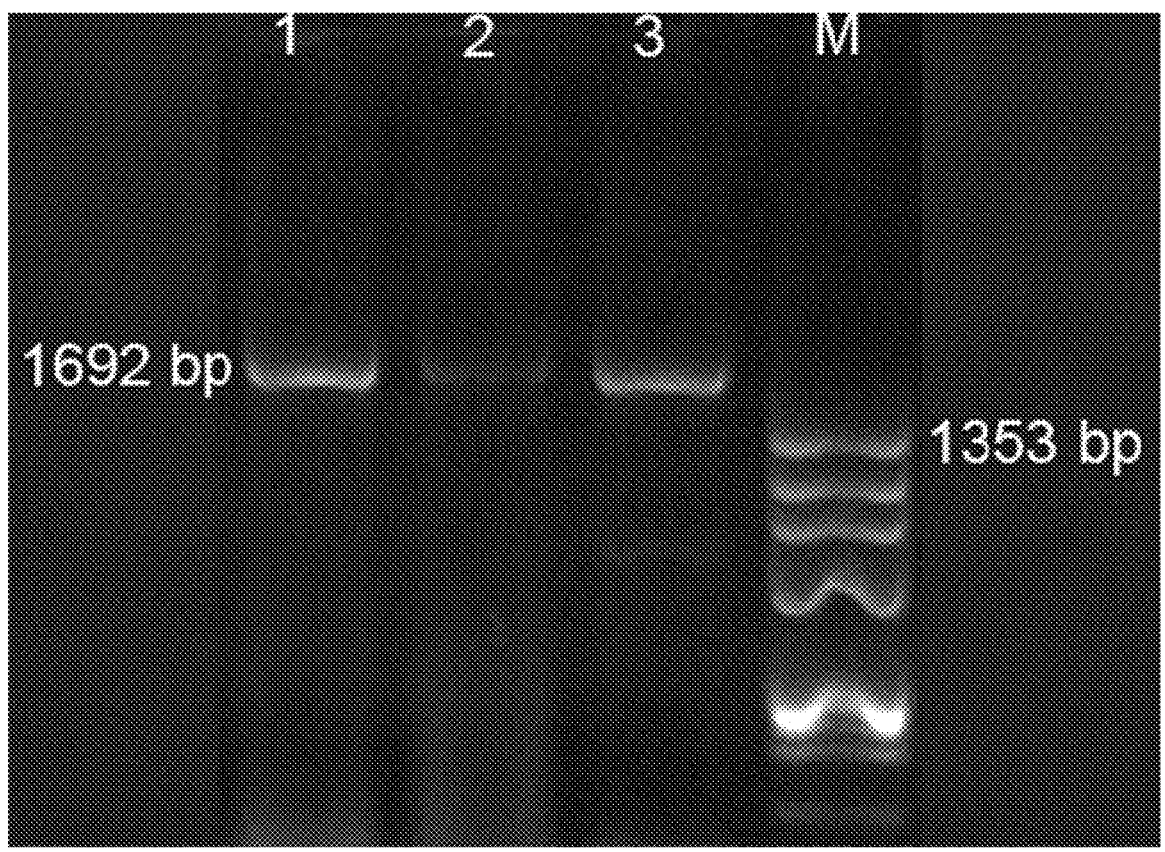
FIG. 8B illustrates results of PCR screening for the recombinant pET-28a (+) cloning vector containing the nucleotide sequence of the anti-MUC18 human immunotoxin in the transformed DH5a *E. coli* colonies using T7 primers, consistent with one or more exemplary embodiments of the present disclosure.

FIG. 8B illustrates results of PCR screening for the recombinant pET-28a (+) cloning vector containing the nucleotide sequence of the anti-MUC18 human immunotoxin in the transformed DH5α *E. coli* colonies using T7 primers, consistent with one or more exemplary embodiments of the present disclosure. Referring to FIG. 8B, presence of a DNA band with a molecular size of about 1692 bp indicates that the tested DH5α *E. coli* colony is a positive clone with the recombinant pET-28a (+) cloning vector containing the nucleotide sequence of the anti-MUC18 human immunotoxin.

After selecting the positive clones containing the nucleotide sequence of the anti-MUC18 human immunotoxin, recombinant pET-28a (+) cloning vector containing the nucleotide sequence of the anti-MUC18 human immunotoxin was extracted from the positive clones and their sequencing was done to confirm the complete homology of the anti-MUC18 human immunotoxin nucleotide sequence. According to the sequencing results, complete homology of the nucleotide sequence of the anti-MUC18 human immunotoxin cloned in the pET-28a (+) cloning vector and a correct reading frame corresponding to the anti-MUC18 human immunotoxin were confirmed.

The extracted pET-28a (+) cloning vector containing the nucleotide sequence of the anti-MUC18 human immunotoxin was used to transform competent BL-21star *E. coli* expression host to induce and produce the anti-MUC18 human immunotoxin. Induction of the anti-MUC18 human immunotoxin was optimized with different concentrations of T7 promoter inducer (isopropyl β-D-1-thiogalactopyranoside (IPTG)), induction times, and temperature.

Induction procedure was as follow. At first, about 50 μl of the recombinant BL-21star stock was inoculated into 5 ml of 2TYG broth medium and incubated in a shaker incubator at a temperature of about 37° C. and at a speed of about 180 rpm overnight. Afterward, culture medium was added to a flask containing about 15 ml of 2TYG broth containing 50 μg/ml kanamycin and incubated for a time period of about 2 hours at a temperature of about 37° C. at a speed of about 200 rpm.

During the incubation when the optical density of the culture at a wavelength of about 600 nm ($OD_{600}$) reached to 0.6, about 1 ml of culture was collected as pre-induction sample and IPTG was added to the remaining culture at different concentrations between 0.5 Mm and 1.5 mM to find the optimum IPTG concentration. The culture was also incubated at 25, 30, and 37° C. to determined optimum temperature.

Figure 9:
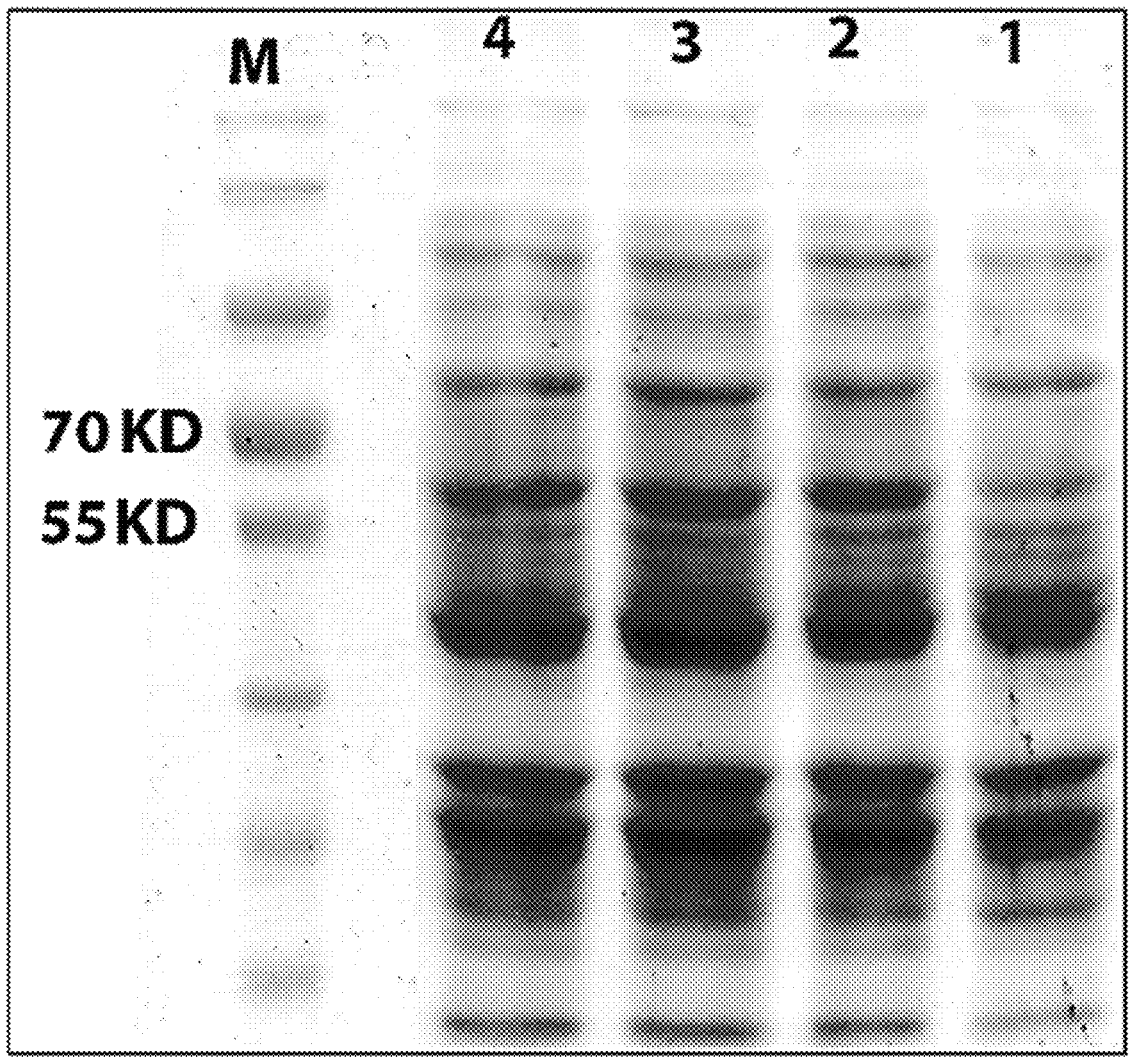
FIG. 9 illustrates SDS-PAGE profile for induction of anti-MUC18 human immunotoxin expression at different IPTG concentrations, pre-incubation (lane 1), post-incubation with 0.5, 1 and 1.5 mM of IPTG (lanes 2, 3 and 4), consistent with one or more exemplary embodiments of the present disclosure.

At different time intervals of 4 hours, 6 hours, and overnight, about 1 ml of culture was sampled, and an equivalent number of cells at each time interval was determined based on $OD_{600}$ of the selected samples and centrifuged to remove supernatants. Then, the bacterial pellets were stored at a temperature of about −20° C. until conducting the SDS-PAGE analysis. FIG. 9 illustrates SDS-PAGE profile for anti-MUC18 human immunotoxin expression at different conditions of pre-induction (lane 1), post-induction sample with 0.5 mM of IPTG (lane 2), post-induction sample with 1 mM of IPTG (lane 3), post-induction sample with 1.5 mM of IPTG (lane 4), consistent with one or more exemplary embodiments of the present disclosure Referring to FIG. 9, SDS-PAGE profiles for expression of the anti-MUC18 human immunotoxin at different incubation times represent a protein band at an expected molecular weight of about 56 KDa. Also, high levels of anti-MUC18 human immunotoxin expression were obtained at an incubation temperature of about 37° C. using about 1 mM and about 1.5 mM IPTG (lanes 3 and 4). Furthermore, expression levels of the anti-MUC18 human immunotoxin were similar at incubation time for 6 hours and overnight.

Example 5: Purification of the Anti-MUC18 Human Immunotoxin

In this example, the anti-MUC18 human immunotoxin which was produced in EXAMPLE 4 was extracted, purified and evaluated. The anti-MUC18 human immunotoxin was extracted from the host cells as follows. At first, about 250 ml of bacterial cell suspension including bacteria which was induced with about 0.5 mM IPTG at 30° C. overnight and expressed the anti-MUC18 human immunotoxin was frozen and thawed at room temperature.

Afterward, the bacterial pellets were lysed by addition of about 1 mg/ml lysozyme in about 8 ml of sodium phosphate buffer for about 30 minutes at a temperature of about 4° C. The bacterial lysates were sonicated six times for about 10 seconds with a cell disruptor and they were centrifuged at a speed of 14000 rounds per minute (rpm) for about 20 minutes at a temperature of about 4° C. The supernatant was transferred and saved on ice, and the sonication procedure was repeated with the cell pellet. Then, supernatants from the two lysates were combined. At the end, the combined supernatants were filtered using a filter with a pore size of about 0.22 μm and a sample including soluble anti-MUC18 human immunotoxin was obtained.

After extraction, the anti-MUC18 human immunotoxin was purified using fast protein liquid chromatography (FPLC). At the beginning of purification procedure, the sample including the soluble anti-MUC18 human immunotoxin was diluted with a binding buffer. Also, the sample including the soluble anti-MUC18 human immunotoxin was filtered through a 0.45 μm filter immediately before loading it to the column in order to prevent clogging and increase the longevity of the column.

Afterward, the column was washed with 1 column volume (CV) distilled water. This step was done to remove the ethanol and avoid precipitation of buffer salts upon exposure to ethanol. Then, the column was equilibrated with at least 5 CV binding buffer until the UV baseline, pH and conductivity were stabled. Afterward, the sample including the soluble anti-MUC18 human immunotoxin was loaded at a flow rate of about 0.5 ml/minutes.

After loading the sample including the soluble anti-MUC18 human immunotoxin, the column was washed with about 5 CV binding buffer until the UV trace of the flow-through returned to near baseline. The column was eluted with a one-step gradient of about 5 CV 100% elution buffer. Finally, fractions were collected into tubes containing about 60 μl of Tris-HCl with a concentration of about 1.0 M and a pH level of about 9.0 per ml of fraction to preserve the activity of anti-MUC18 HscFv because the elution buffer had very low pH. Moreover, the elution buffer was exchanged with phosphate-buffered saline (PBS) using dialysis procedure overnight to remove small and unwanted molecules in the solution. The purified protein was aliquoted and stored at a temperature of about −20° C.

Figure 10A:
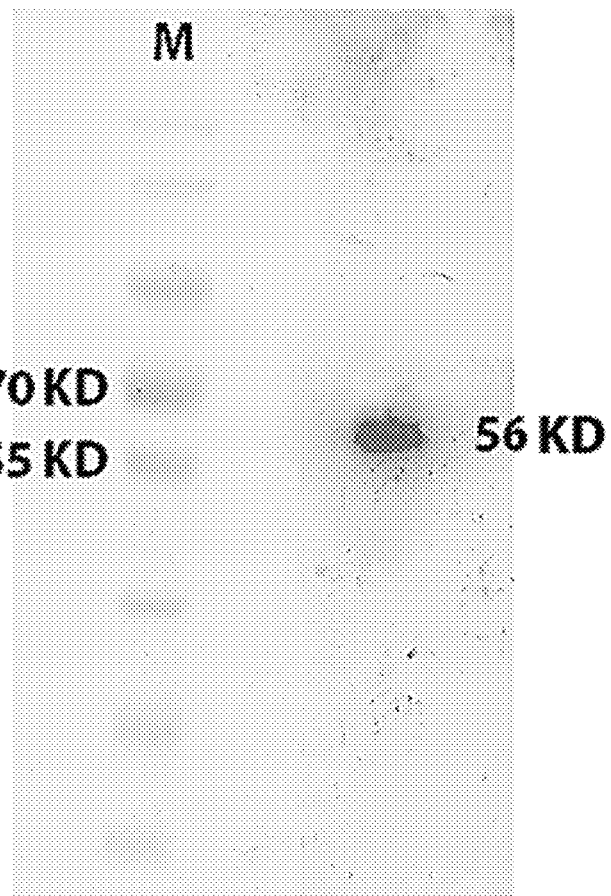
FIG. 10A illustrates an SDS-PAGE profile of purified protein of anti-MUC18 human immunotoxin, consistent with one or more exemplary embodiments of the present disclosure.

After conducting FPLC, sodium dodecyl sulfate-polyacrylamide gel electrophoresis (SDS-PAGE) analysis of the collected fractions of the anti-MUC18 human immunotoxin was done and the purified human immunotoxin was evaluated using western blot analysis. FIG. 10A shows an SDS-PAGE profile of the purified protein of anti-MUC18 human immunotoxin, consistent with one or more exemplary embodiments of the present disclosure. The SDS-PAGE analysis was performed using a 10% polyacrylamide gel followed by COOMASSIE BLUE staining. Referring to FIG. 10A, the SDS-PAGE profile of the anti-MUC18 human immunotoxin purified by FPLC shows a highly pure protein band with a molecular size of about 56 kDa.

Figure 10B:
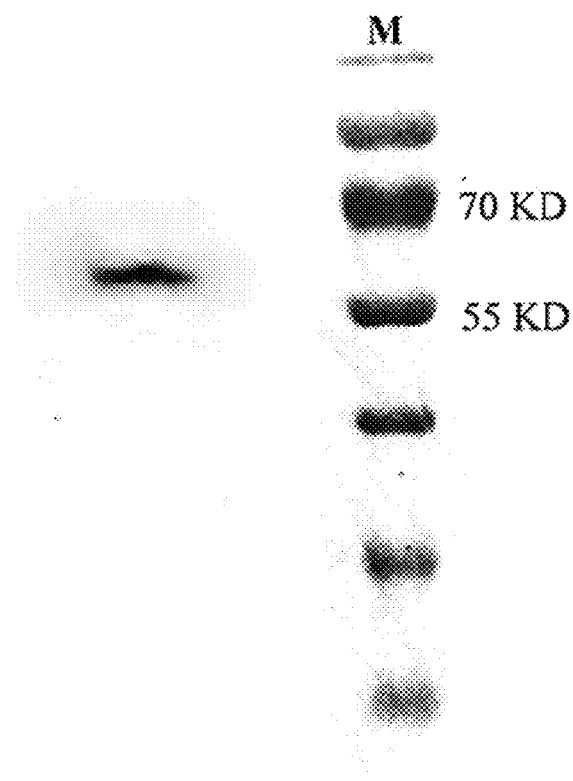
FIG. 10B illustrates a western blot profile of anti-MUC18 human immunotoxin, consistent with one or more exemplary embodiments of the present disclosure.

Also, the identity of the purified proteins was evaluated by western blot assay using a rabbit anti-PEA antibody. FIG. 10B shows a western blot profile of the anti-MUC18 human immunotoxin, consistent with one or more exemplary embodiments of the present disclosure. Western blot analysis of the anti-MUC18 human immunotoxin was performed using a commercial rabbit anti-PEA toxin. Referring to FIG. 10B, the western blot profile of the anti-MUC18 human immunotoxin shows specific reactivity of the anti-MUC18 human immunotoxin with the anti-PEA antibody in immunoblotting.

Figure 11:
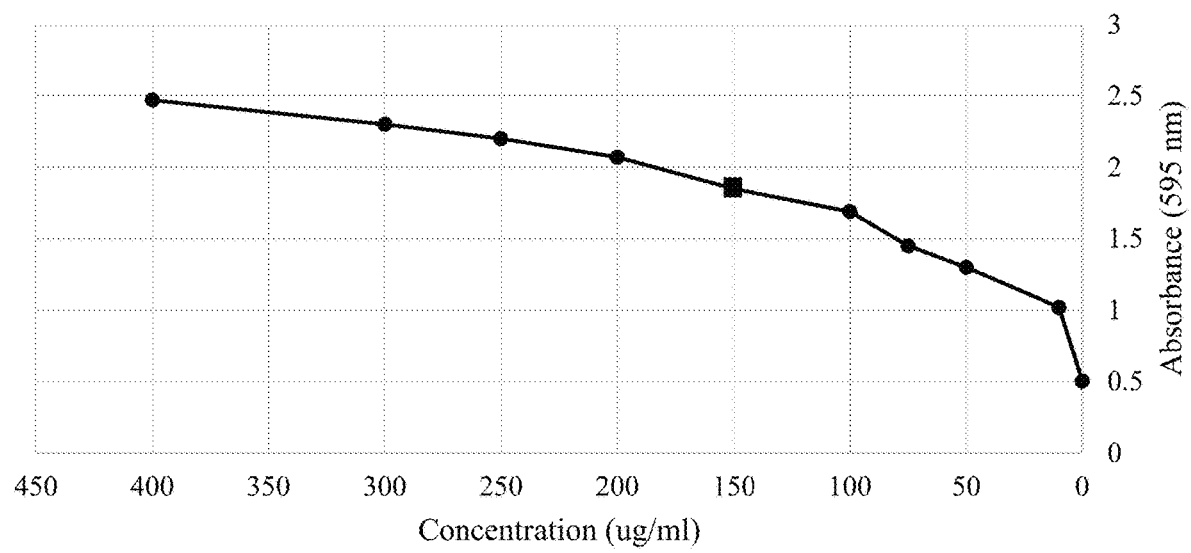
FIG. 11 illustrates a standard curve of Bradford assay of anti-MUC18 human immunotoxin, consistent with one or more exemplary embodiments of the present disclosure.

After purification of the anti-MUC18 human immunotoxin, concentration of the anti-MUC18 human immunotoxin solution was determined using Bradford assay. FIG. 11 shows a standard curve of the Bradford assay which was provided based on optical densities (ODs) obtained at a wavelength of about 595 nm from eight different concentrations between 0 and 400 μg/ml bovine serum albumin (BSA) standards, consistent with one or more exemplary embodiments of the present disclosure. Referring to FIG. 11 concentration of the anti-MUC18 human immunotoxin was about 150 μg/ml.

Example 6: Cell Binding Assay of the Anti-MUC18 Human Immunotoxin

In this example, cell binding assay of the anti-MUC18 human immunotoxin was investigated. Cell surface binding capacities of the anti-MUC18 human immunotoxin were determined by flow cytometry analysis in comparison with a commercial anti-MUC18 monoclonal antibody. At first, about $5 \times 10^5$ cells of DU145, A375, and SKBR3 cell lines were incubated with about 800 ng/ml of anti-MUC18 human immunotoxin for about 35 min at a temperature of about 4° C. in dark place. Afterward, the cells were washed three times with complete RPMI 1640 media. Moreover, as an isotype control, cells were treated with an anti-M13 antibody.

In the next step, a rabbit anti-PEA antibody with a dilution of about 1/500 was added to cells and incubated at room temperature for about 40 minutes. The cells were washed three times with complete media and stained with 1/500 dilution of PE-conjugated anti-rabbit antibody. At the end, amounts of anti-MUC18 human immunotoxin and anti-MUC18 HscFv which were bound to the cells were measured by the FACS Calibur as a fluorescence-activated cell sorter.

Figure 12:
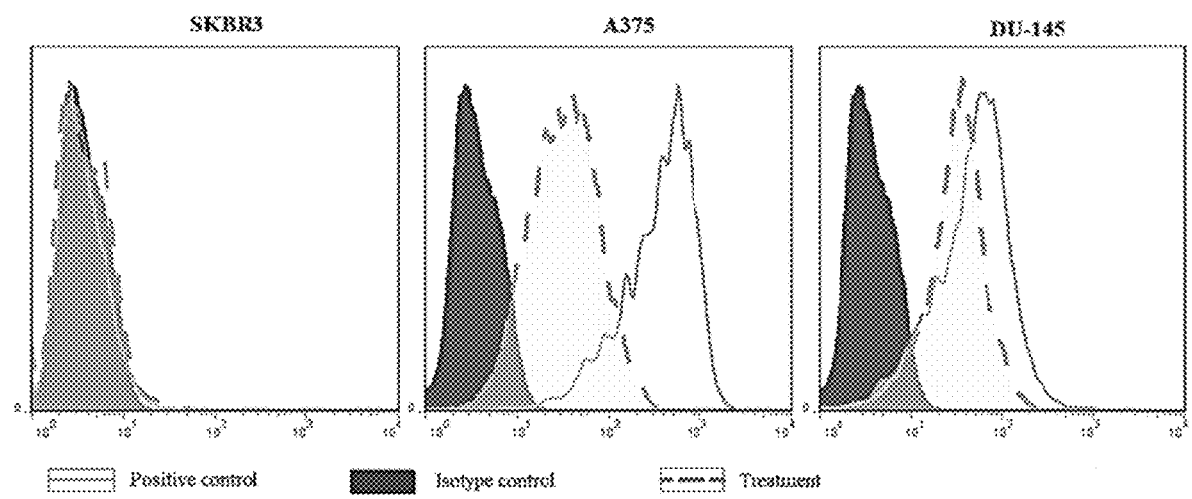
FIG. 12 illustrates flow cytometry histograms of cell binding of anti-MUC18 human immunotoxin to different cell lines, consistent with one or more exemplary embodiments of the present disclosure.

FIG. 12 shows flow cytometry histograms of cell binding of the anti-MUC18 human immunotoxin to different cells, consistent with one or more exemplary embodiments of the present disclosure. Referring to FIG. 12, there is no significant shift in fluorescent intensity of different cells treated with the anti-M13 antibody as the isotype control. In the treatment group, the anti-MUC18 human immunotoxin was bound to about 88.2% of A375 cells and about 71.7% of DU145 cells. Also, the anti-MUC18 human immunotoxin was bound to about 1.05% of SKBR3 cells which indicates that the exemplary anti-MUC18 human immunotoxin of the present disclosure can specifically bind to MUC18-positive cells.

Moreover, in the positive control, the commercial anti-MUC18 antibody is bound to 84.8% of DU145 cells, 99.3% of A375 cells, and 1.9% of SKBR3 cells as a negative control. Therefore, there is no significant shift in fluorescent intensity of SKBR3 cells because SKBR3 cells are MUC18-negative cells.

Example 7: Cytotoxicity Assay of the Anti-MUC18 Human Immunotoxin

In this example, cytotoxicity and anti-proliferative effects of the anti-MUC18 human immunotoxin were evaluated in a (3-(4,5-dimethylthiazol-2-yl)-2,5-diphenyltetrazolium bromide) MTT assay. At first, A375 cell line as a melanoma cancer cells and DU145 cell line as prostate cancer cells were separately seeded into a 96-well flat-bottomed plate. The cells were then treated with different concentrations of the anti-MUC18 human immunotoxin at a temperature of about 37° C. for about 24 hours.

Figure 13:
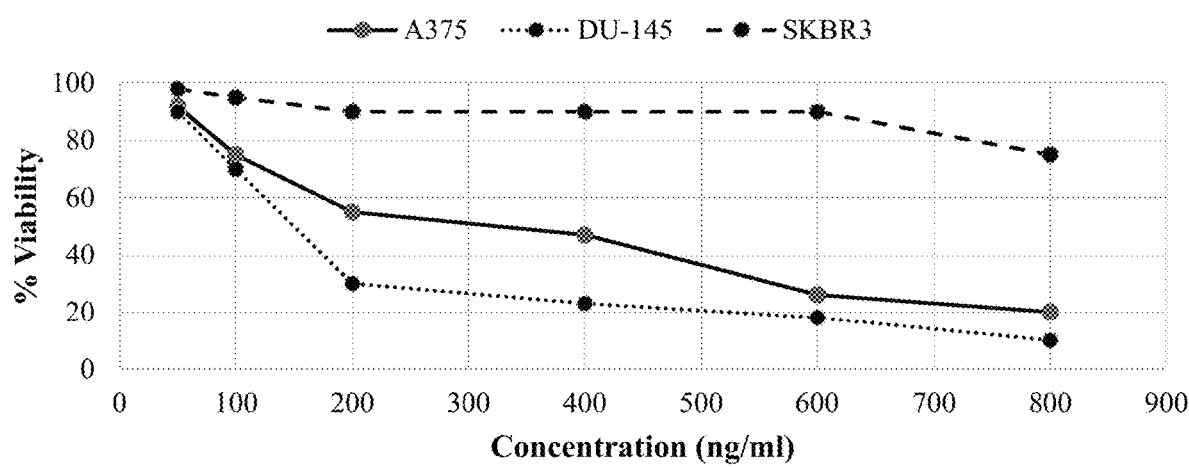
FIG. 13 illustrates viability of cells at different concentrations of purified anti-MUC18 human immunotoxin, consistent with one or more exemplary embodiments of the present disclosure.

The concentrations of the anti-MUC18 human immunotoxin were 0, 50 ng/ml, 100 ng/ml, 200 ng/ml, 400 ng/ml, 600 ng/ml, and 800 ng/ml. Also, SKBR3 cell line was employed as a negative control. Afterward, MTT reagents were aspirated and residual crystals were solved by 100 μl of DMSO. Then, the cells were incubated with about 100 μL of MTT reagent for about 4 hours at a temperature of about 37° C., and the absorbance of each well was read at a wavelength of 570 nm using a plate reader. FIG. 13 shows viability of cells at different concentrations of purified anti-MUC18 human immunotoxin, consistent with one or more exemplary embodiments of the present disclosure.

Referring to FIG. 13, the anti-MUC18 human immunotoxin at a concentration of about 800 ng/ml inhibits the growth of 90% of A375 cells and 80% of DU145 cells. The IC50 of the anti-MUC18 human immunotoxin was about 2.1 nM for A375 cells, and about 6.1 nM for DU145 cells. Therefore, the anti-MUC18 human immunotoxin has a high anti-proliferative and cytotoxic activity against A375 and DU145 cell lines. Moreover, SKBR3 cells as a negative control were less sensitive to the anti-MUC18 human immunotoxin and only 25% growth inhibition was observed for SKBR3 cells at a similar concentration of anti-MUC18 human immunotoxin which was about 800 ng/ml which represents the selective cytotoxicity of anti-MUC18 human immunotoxin on MUC18 bearing cells.

Figure 14:
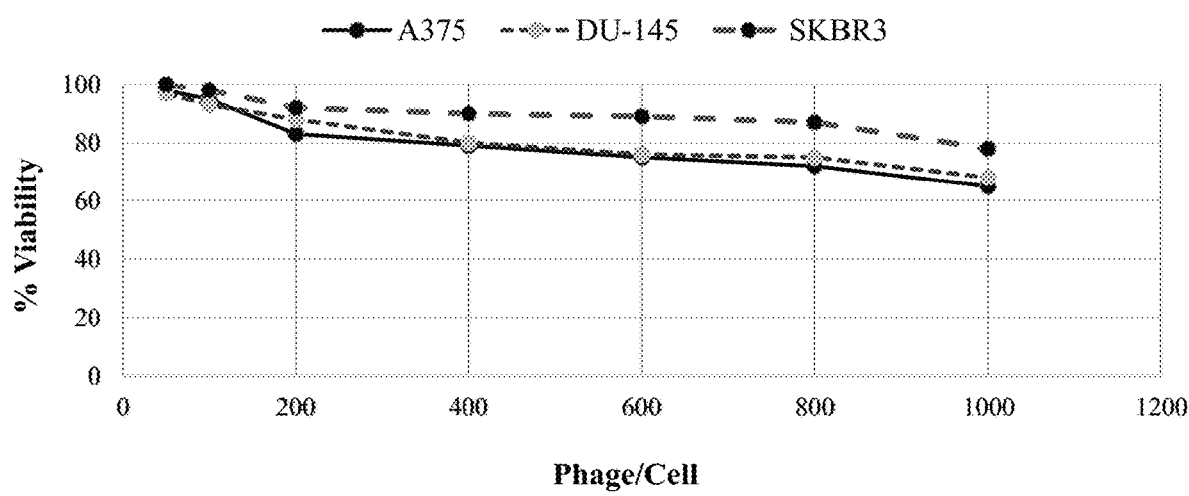
FIG. 14 illustrates viability of cells at different densities of anti-MUC18 HscFv-displaying phages, consistent with one or more exemplary embodiments of the present disclosure.

Furthermore, in order to evaluate the anti-proliferative effect of the anti-MUC18 HscFv on A375 and DU145 cell lines, the MTT assay was done using anti-MUC18 HscFv-displaying phages. FIG. 14 shows viability of cells at different densities of anti-MUC18 HscFv-displaying phages, consistent with one or more exemplary embodiments of the present disclosure.

Referring to FIG. 14, the anti-MUC18 HscFv-displaying phages with a density up to about 1000 phage/cell have about 25% anti-proliferative and cytotoxic effect on A375 cell line and about 23% anti-proliferative and cytotoxic effect on DU145 cell line. It should be noted that A375 and DU145 cell lines are MUC18-expressing cell lines. Although the anti-MUC18 HscFv showed some cytotoxicity effect alone, the majority of cytotoxic effect was due to presence of PEA in the composition of anti-MUC18 human immunotoxin.

Example 8: Apoptosis Assay of the Anti-MUC18 Human Immunotoxin

Apoptosis or programmed cell death (PCD) is a genetically encoded cell elimination program which ensures the equilibrium between cell proliferation and cell death. In apoptosis, damaged or unwanted cells are eliminated. In this example, apoptosis assay of the anti-MUC18 human immunotoxin was assessed as follows in three groups of untreated group, treated group, and positive control group.

A calcium buffer was diluted about 20 times in distilled water and kept at a temperature of about 4° C., and about $10^5$ cells/ml of interested cells were seeded in a 6-well plate. The interested cells were A375 cell line as a melanoma cancer cells and DU145 cell line as prostate cancer cells. Afterward, the seeded cells were treated with a solution of anti-MUC18 human immunotoxin with a concentration of about 800 ng/ml for a time period of about 24 hours at a temperature of about 37° C. in a $CO_2$ incubator. Also, a positive control was prepared by adding about 50 μL of dimethyl sulfoxide (DMSO) as an apoptosis inducer to the seeded cell of one well.

In the next step, a cell suspension was formed by detaching cells of each well, and adding about 2 volumes of calcium buffer. The cell suspension was twice centrifuged for about 3 minutes with a G-force of about 400 g. After centrifugation, in order to stain cells, about 10 μl of Annexin V-fluorescein isothiocyanate (FITC) was added to about 100 μl of cell suspension and incubated for about 20 minutes at a temperature about 4° C.

Figure 15:
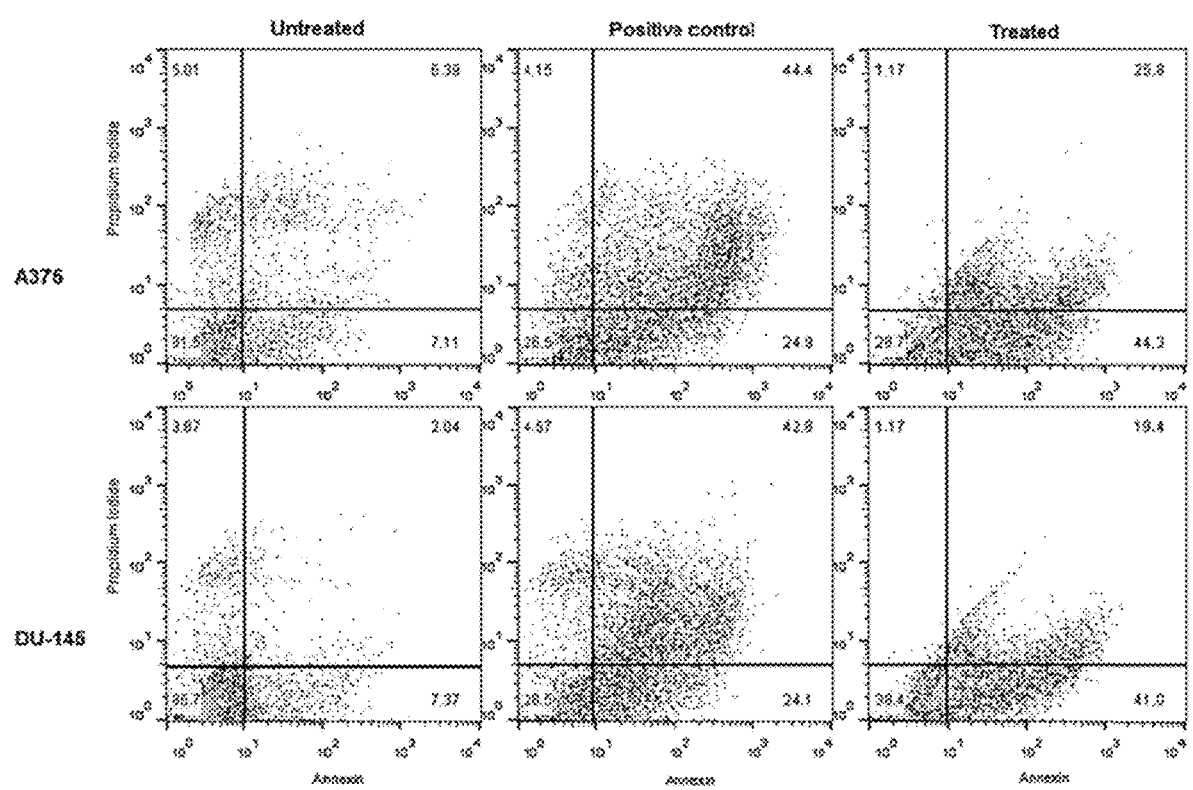
FIG. 15 illustrates Annexin V versus propidium iodide (PI) plots of the gated cells after apoptosis assay, consistent with one or more exemplary embodiments of the present disclosure.

The cells were washed again with about 2 volumes of calcium buffer for about 3 minutes at a G-force of about 400 g. Then, the washed cells were incubated with about 10 μl of propidium iodide for a time period of about 10 minutes at a temperature of about 4° C. Finally, the apoptosis rate of the cells was analyzed by fluorescence-activated cell sorting (FACS) method, and Annexin V versus PI plots of the gated cells were obtained. The Annexin V versus PI plot of the gated cells shows the populations of cells corresponding to viable and non-apoptotic (Annexin V−/PI−), early (Annexin V+/PI−), and late (Annexin V+/PI+) apoptotic cells. FIG. 15 shows Annexin V versus PI plots of the gated cells after the apoptosis assay, consistent with one or more exemplary embodiments of the present disclosure.

Referring to FIG. 15, in the untreated group, the minority of cells were apoptotic, characterized as early (Annexin V+/PI−), and late (Annexin V+/PI+) apoptotic cell populations, 13% for A375 and 9% for DU-145 cell lines, and the majority of cells were viable and non-apoptotic because they show Annexin V negative and PI negative profile (Annexin V−/PI−). However, in the treated group, about 71% of A375 cells and 62% of DU145 cells treated with anti-MUC18 human immunotoxin undergo apoptosis cell death. Also, nominal amounts of treated cells (1.17%) were detected as Annexin V−/PI+ corresponding to necrotic cell populations. Therefore, treatment of cells with anti-MUC18 human immunotoxin leads the majority of cells towards apoptosis.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claim.

What is claimed is:

1. An anti-MUC18 human immunotoxin, comprising:
   an anti-MUC18 human single-chain variable fragment (anti-MUC18 HscFv) comprising SEQ ID NO: 4; and
   a truncated *Pseudomonas* exotoxin A (PEA) comprising SEQ ID NO: 6, the truncated PEA genetically fused to the anti-MUC18 HscFv through a connector.

2. The anti-MUC18 human immunotoxin according to claim 1, wherein the anti-MUC18 human immunotoxin comprises SEQ ID NO: 2.

3. The anti-MUC18 human immunotoxin according to claim 2, wherein the anti-MUC18 human immunotoxin comprises SEQ ID NO: 2 encoded by SEQ ID NO: 1.

4. The anti-MUC18 human immunotoxin according to claim 1, wherein the anti-MUC18 HscFv comprises SEQ ID NO: 4 encoded by SEQ ID NO: 3.

5. The anti-MUC18 human immunotoxin according to claim 1, wherein the truncated PEA comprises 259 residues from the C-terminal of a mature *Pseudomonas* exotoxin A (PEA), the truncated PEA comprising:
   a furin cleavage site comprising SEQ ID NO: 21;
   a domain Ib of PEA comprising SEQ ID NO: 22;
   a domain III of PEA comprising SEQ ID NO: 23; and
   a carboxyl terminal region comprising SEQ ID NO: 24.

6. The anti-MUC18 human immunotoxin according to claim 1, wherein the truncated PEA comprises SEQ ID NO: 6 encoded by SEQ ID NO: 5.

7. The anti-MUC18 human immunotoxin according to claim 1, wherein the connector comprises SEQ ID NO: 8 encoded by SEQ ID NO: 7.

8. The anti-MUC18 human immunotoxin according to claim 1, wherein the anti-MUC18 HscFv is against an immunodominant epitope of MUC18 as set forth in SEQ ID NO: 25.

9. The anti-MUC18 human immunotoxin according to claim 1, wherein the HscFv comprises:
   a variable heavy (VH) chain encoded by SEQ ID NO: 9, and
   a variable light (VL) chain encoded by SEQ ID NO: 11, the VH chain connected to the VL chain with a linker, wherein the linker comprises SEQ ID NO: 14.

10. The anti-MUC18 human antibody according to claim 9, wherein the linker comprises SEQ ID NO: 14 encoded by SEQ ID NO: 13.

* * * * *

SEQUENCE LISTING

<160> NUMBER OF SEQ ID NOS: 25

<210> SEQ ID NO 1
<211> LENGTH: 1530
<212> TYPE: DNA
<213> ORGANISM: Artificial Sequence
<220> FEATURE:
<223> OTHER INFORMATION: Sequence of human anti-MUC18 immunotoxin
<220> FEATURE:
<221> NAME/KEY: CDS
<222> LOCATION: (1)..(1530)

<400> SEQUENCE: 1

```
ggc cga ggt gca ctg gtg gag tct ggc cca gga ctg gtg aag cct tcg      48
Gly Arg Gly Ala Leu Val Glu Ser Gly Pro Gly Leu Val Lys Pro Ser
1               5                   10                  15 gag acc ctg ttc ctc acc tgc act gtc tct ggt ggc tcc atc agt tct      96
Glu Thr Leu Phe Leu Thr Cys Thr Val Ser Gly Gly Ser Ile Ser Ser
                20                  25                  30 tac tac tgg agc tgg atc cgg cag ccc gca ggg aag gga ctg gag tgg     144
Tyr Tyr Trp Ser Trp Ile Arg Gln Pro Ala Gly Lys Gly Leu Glu Trp
            35                  40                  45 att gcg tat atc tat tac agt ggg agc acc aac tac aac ccc tcc ctc     192
Ile Ala Tyr Ile Tyr Tyr Ser Gly Ser Thr Asn Tyr Asn Pro Ser Leu
        50                  55                  60 aag agt cga gtc acc ata tca gta gac acg tcc aac aac cag ttc tcc     240
Lys Ser Arg Val Thr Ile Ser Val Asp Thr Ser Asn Asn Gln Phe Ser
65                  70                  75                  80 ctg aaa ctg agc tct gtg acc gct gcg gac acg gcc gtg tat tat tgt     288
Leu Lys Leu Ser Ser Val Thr Ala Ala Asp Thr Ala Val Tyr Tyr Cys
                85                  90                  95 gcg aag tta aca gca gcc ggg ggc cac ttc gac ccc tgg ggc cag ggc     336
Ala Lys Leu Thr Ala Ala Gly Gly His Phe Asp Pro Trp Gly Gln Gly
                100                 105                 110 acc ctg gtc acc gtc tcc tca ggt gga ggc ggt tca ggc gga ggt ggc     384
Thr Leu Val Thr Val Ser Ser Gly Gly Gly Gly Ser Gly Gly Gly Gly
            115                 120                 125 agc ggc ggt ggc gga tcg gac atc gtg atg acc cag tct cca tcc tcc     432
Ser Gly Gly Gly Gly Ser Asp Ile Val Met Thr Gln Ser Pro Ser Ser
        130                 135                 140
```

-continued

| | | |
|---|---|---|
| ctg tct gca tct ata ggg gac aga gtc acc atc act tgt cgg gca agt<br>Leu Ser Ala Ser Ile Gly Asp Arg Val Thr Ile Thr Cys Arg Ala Ser<br>145                        150                        155                      160 | | 480 |
| cag ggc att agc aat ttt tta gcc tgg ttt cag cag aaa cca ggg aaa<br>Gln Gly Ile Ser Asn Phe Leu Ala Trp Phe Gln Gln Lys Pro Gly Lys<br>                  165                        170                        175 | | 528 |
| gcc cct aag tcc ctg atc tat gct gca tcc agt ttg caa agt ggg gtc<br>Ala Pro Lys Ser Leu Ile Tyr Ala Ala Ser Ser Leu Gln Ser Gly Val<br>        180                        185                        190 | | 576 |
| cca tca agg ttc agc ggc agt gga tct ggg aca gat ttc act ctc gcc<br>Pro Ser Lys Phe Ser Gly Ser Gly Ser Gly Thr Asp Phe Thr Leu Ala<br>195                        200                        205 | | 624 |
| atc agc agc ctg cag cct gaa gat ttt gca act tat tac tgt ctc caa<br>Ile Ser Ser Leu Gln Pro Glu Asp Phe Ala Thr Tyr Tyr Cys Leu Gln<br>        210                        215                        220 | | 672 |
| gat tcc gat tat cct ctc act ttc ggc gga ggg acc aag ctg gag atc<br>Asp Ser Asp Tyr Pro Leu Thr Phe Gly Gly Gly Thr Lys Leu Glu Ile<br>225                        230                        235                        240 | | 720 |
| aaa cgt gct agc ggc ggc ccg gaa ggc ggc agc cgc cat cgt cag ccg<br>Lys Arg Ala Ser Gly Gly Pro Glu Gly Gly Ser Arg His Arg Gln Pro<br>                  245                        250                        255 | | 768 |
| cgt ggc tgg gaa cag ctg gca gac gtg gtt tcc ctg acc tgt ccg gtt<br>Arg Gly Trp Glu Gln Leu Ala Asp Val Val Ser Leu Thr Cys Pro Val<br>        260                        265                        270 | | 816 |
| gct gcg ggc gaa tgt gcg ggt ccg gca gat tcc ggt gat gca ctg ctg<br>Ala Ala Gly Glu Cys Ala Gly Pro Ala Asp Ser Gly Asp Ala Leu Leu<br>275                        280                        285 | | 864 |
| gaa cgt aac tat ccg acc ggc gcc gaa ttt ctg ggt gat ggc ggt gca<br>Glu Arg Asn Tyr Pro Thr Gly Ala Glu Phe Leu Gly Asp Gly Gly Ala<br>        290                        295                        300 | | 912 |
| att tca ttc tcg acc cgc ggc acg cag aat tgg acg gtg gaa cgt ctg<br>Ile Ser Phe Ser Thr Arg Gly Thr Gln Asn Trp Thr Val Glu Arg Leu<br>305                        310                        315                        320 | | 960 |
| ctg caa gcc cat cgc caa ctg gaa gaa ggc ggt tat gtt ttt gtc ggc<br>Leu Gln Ala His Arg Gln Leu Glu Glu Gly Gly Tyr Val Phe Val Gly<br>                  325                        330                        335 | | 1008 |
| tat cat ggc acc ttt ctg gaa gcc gca cag tca atc gtg ttt ggc ggt<br>Tyr His Gly Thr Phe Leu Glu Ala Ala Gln Ser Ile Val Phe Gly Gly<br>        340                        345                        350 | | 1056 |
| gtt cgt gcg cgc tcg cag gat ctg gat gct att tgg gcg ggc ttc tac<br>Val Arg Ala Arg Ser Gln Asp Leu Asp Ala Ile Trp Ala Gly Phe Tyr<br>355                        360                        365 | | 1104 |
| atc gcc ggt gat ccg gcg ctg gcg tat ggc tac gca cag gat caa gaa<br>Ile Ala Gly Asp Pro Ala Leu Ala Tyr Gly Tyr Ala Gln Asp Gln Glu<br>        370                        375                        380 | | 1152 |
| ccg gac gct gcg ggc cgt att cgc aac ggt gcg ctg ctg cgt gtg tat<br>Pro Asp Ala Ala Gly Arg Ile Arg Asn Gly Ala Leu Leu Arg Val Tyr<br>385                        390                        395                        400 | | 1200 |
| gtt ccg cgc agc tct ctg ccg ggc ttt tat gca acc ggt ctg acg ctg<br>Val Pro Arg Ser Ser Leu Pro Gly Phe Tyr Ala Thr Gly Leu Thr Leu<br>                  405                        410                        415 | | 1248 |
| gcc gca ccg gaa gct gcg ggc gaa gtg gaa cgt ctg att ggt cac ccg<br>Ala Ala Pro Glu Ala Ala Gly Glu Val Glu Arg Leu Ile Gly His Pro<br>        420                        425                        430 | | 1296 |
| ctg ccg ctg cgc ctg gat gct atc acc ggt ccg gaa gaa gcg ggc ggt<br>Leu Pro Leu Arg Leu Asp Ala Ile Thr Gly Pro Glu Glu Ala Gly Gly<br>435                        440                        445 | | 1344 |
| cgt ctg gaa acg att ctg ggt tgg ccg ctg gct gaa cgc acc gtc gtg<br>Arg Leu Glu Thr Ile Leu Gly Trp Pro Leu Ala Glu Arg Thr Val Val | | 1392 |

```
                  450                 455                 460
att ccg agc gcg atc ccg acc gat ccg cgt aat gtt ggc ggt gat ctg       1440
Ile Pro Ser Ala Ile Pro Thr Asp Pro Arg Asn Val Gly Gly Asp Leu
465                 470                 475                 480 gac ccg agt tcc atc ccg gac tct gaa gcc gca atc tca gcc ctg ccg       1488
Asp Pro Ser Ser Ile Pro Asp Ser Glu Ala Ala Ile Ser Ala Leu Pro
                    485                 490                 495 gat tat gcc agc caa ccg ggt aaa ccg ccg aaa gac gaa ctg               1530
Asp Tyr Ala Ser Gln Pro Gly Lys Pro Pro Lys Asp Glu Leu
                500                 505                 510

<210> SEQ ID NO 2
<211> LENGTH: 510
<212> TYPE: PRT
<213> ORGANISM: Artificial Sequence
<220> FEATURE:
<223> OTHER INFORMATION: Synthetic Construct

<400> SEQUENCE: 2

Gly Arg Gly Ala Leu Val Glu Ser Gly Pro Gly Leu Val Lys Pro Ser
1               5                   10                  15

Glu Thr Leu Phe Leu Thr Cys Thr Val Ser Gly Gly Ser Ile Ser Ser
                20                  25                  30

Tyr Tyr Trp Ser Trp Ile Arg Gln Pro Ala Gly Lys Gly Leu Glu Trp
            35                  40                  45

Ile Ala Tyr Ile Tyr Tyr Ser Gly Ser Thr Asn Tyr Asn Pro Ser Leu
        50                  55                  60

Lys Ser Arg Val Thr Ile Ser Val Asp Thr Ser Asn Asn Gln Phe Ser
65                  70                  75                  80

Leu Lys Leu Ser Ser Val Thr Ala Ala Asp Thr Ala Val Tyr Tyr Cys
                85                  90                  95

Ala Lys Leu Thr Ala Ala Gly Gly His Phe Asp Pro Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asp Ile Val Met Thr Gln Ser Pro Ser Ser
130                 135                 140

Leu Ser Ala Ser Ile Gly Asp Arg Val Thr Ile Thr Cys Arg Ala Ser
145                 150                 155                 160

Gln Gly Ile Ser Asn Phe Leu Ala Trp Phe Gln Lys Pro Gly Lys
                165                 170                 175

Ala Pro Lys Ser Leu Ile Tyr Ala Ala Ser Ser Leu Gln Ser Gly Val
            180                 185                 190

Pro Ser Lys Phe Ser Gly Ser Gly Ser Gly Thr Asp Phe Thr Leu Ala
        195                 200                 205

Ile Ser Ser Leu Gln Pro Glu Asp Phe Ala Thr Tyr Tyr Cys Leu Gln
    210                 215                 220

Asp Ser Asp Tyr Pro Leu Thr Phe Gly Gly Thr Lys Leu Glu Ile
225                 230                 235                 240

Lys Arg Ala Ser Gly Gly Pro Glu Gly Gly Ser Arg His Arg Gln Pro
                245                 250                 255

Arg Gly Trp Glu Gln Leu Ala Asp Val Val Ser Leu Thr Cys Pro Val
            260                 265                 270

Ala Ala Gly Glu Cys Ala Gly Pro Ala Asp Ser Gly Asp Ala Leu Leu
        275                 280                 285

Glu Arg Asn Tyr Pro Thr Gly Ala Glu Phe Leu Gly Asp Gly Gly Ala
```

-continued

```
                    290                 295                 300
Ile Ser Phe Ser Thr Arg Gly Thr Gln Asn Trp Thr Val Glu Arg Leu
305                 310                 315                 320

Leu Gln Ala His Arg Gln Leu Glu Glu Gly Tyr Val Phe Val Gly
                325                 330                 335

Tyr His Gly Thr Phe Leu Glu Ala Ala Gln Ser Ile Val Phe Gly Gly
                340                 345                 350

Val Arg Ala Arg Ser Gln Asp Leu Asp Ala Ile Trp Ala Gly Phe Tyr
                355                 360                 365

Ile Ala Gly Asp Pro Ala Leu Ala Tyr Gly Tyr Ala Gln Asp Gln Glu
            370                 375                 380

Pro Asp Ala Ala Gly Arg Ile Arg Asn Gly Ala Leu Leu Arg Val Tyr
385                 390                 395                 400

Val Pro Arg Ser Ser Leu Pro Gly Phe Tyr Ala Thr Gly Leu Thr Leu
                405                 410                 415

Ala Ala Pro Glu Ala Ala Gly Glu Val Glu Arg Leu Ile Gly His Pro
                420                 425                 430

Leu Pro Leu Arg Leu Asp Ala Ile Thr Gly Pro Glu Glu Ala Gly Gly
                435                 440                 445

Arg Leu Glu Thr Ile Leu Gly Trp Pro Leu Ala Glu Arg Thr Val Val
                450                 455                 460

Ile Pro Ser Ala Ile Pro Thr Asp Pro Arg Asn Val Gly Gly Asp Leu
465                 470                 475                 480

Asp Pro Ser Ser Ile Pro Asp Ser Glu Ala Ala Ile Ser Ala Leu Pro
                485                 490                 495

Asp Tyr Ala Ser Gln Pro Gly Lys Pro Pro Lys Asp Glu Leu
                500                 505                 510

<210> SEQ ID NO 3
<211> LENGTH: 726
<212> TYPE: DNA
<213> ORGANISM: Homo sapiens
<220> FEATURE:
<221> NAME/KEY: CDS
<222> LOCATION: (1)..(726)

<400> SEQUENCE: 3 ggt cga ggt gca ctg gtg gag tct ggc cca gga ctg gtg aag cct tcg       48
Gly Arg Gly Ala Leu Val Glu Ser Gly Pro Gly Leu Val Lys Pro Ser
1               5                   10                  15 gag acc ctg ttc ctc acc tgc act gtc tct ggt ggc tcc atc agt tct       96
Glu Thr Leu Phe Leu Thr Cys Thr Val Ser Gly Gly Ser Ile Ser Ser
            20                  25                  30 tac tac tgg agc tgg atc cgg cag ccc gca ggg aag gga ctg gag tgg      144
Tyr Tyr Trp Ser Trp Ile Arg Gln Pro Ala Gly Lys Gly Leu Glu Trp
        35                  40                  45 att gcg tat atc tat tac agt ggg agc acc aac tac aac ccc tcc ctc      192
Ile Ala Tyr Ile Tyr Tyr Ser Gly Ser Thr Asn Tyr Asn Pro Ser Leu
    50                  55                  60 aag agt cga gtc acc ata tca gta gac acg tcc aac aac cag ttc tcc      240
Lys Ser Arg Val Thr Ile Ser Val Asp Thr Ser Asn Asn Gln Phe Ser
65                  70                  75                  80 ctg aaa ctg agc tct gtg acc gct gcg gac acg gcc gtg tat tat tgt      288
Leu Lys Leu Ser Ser Val Thr Ala Ala Asp Thr Ala Val Tyr Tyr Cys
                85                  90                  95 gcg aag tta aca gca gcc ggg ggc cac ttc gac ccc tgg ggc cag ggc      336
Ala Lys Leu Thr Ala Ala Gly Gly His Phe Asp Pro Trp Gly Gln Gly
            100                 105                 110
```

```
acc ctg gtc acc gtc tcc tca ggt gga ggc ggt tca ggc gga ggt ggc      384
Thr Leu Val Thr Val Ser Ser Gly Gly Gly Gly Ser Gly Gly Gly Gly
            115                 120                 125 agc ggc ggt ggc gga tcg gac atc gtg atg acc cag tct cca tcc tcc      432
Ser Gly Gly Gly Gly Ser Asp Ile Val Met Thr Gln Ser Pro Ser Ser
    130                 135                 140 ctg tct gca tct ata ggg gac aga gtc acc atc act tgt cgg gca agt      480
Leu Ser Ala Ser Ile Gly Asp Arg Val Thr Ile Thr Cys Arg Ala Ser
145                 150                 155                 160 cag ggc att agc aat ttt tta gcc tgg ttt cag cag aaa cca ggg aaa      528
Gln Gly Ile Ser Asn Phe Leu Ala Trp Phe Gln Gln Lys Pro Gly Lys
                165                 170                 175 gcc cct aag tcc ctg atc tat gct gca tcc agt ttg caa agt ggg gtc      576
Ala Pro Lys Ser Leu Ile Tyr Ala Ala Ser Ser Leu Gln Ser Gly Val
            180                 185                 190 cca tca aag ttc agc ggc agt gga tct ggg aca gat ttc act ctc gcc      624
Pro Ser Lys Phe Ser Gly Ser Gly Ser Gly Thr Asp Phe Thr Leu Ala
        195                 200                 205 atc agc agc ctg cag cct gaa gat ttt gca act tat tac tgt ctc caa      672
Ile Ser Ser Leu Gln Pro Glu Asp Phe Ala Thr Tyr Tyr Cys Leu Gln
210                 215                 220 gat tcc gat tat cct ctc act ttc ggc gga ggg acc aag ctg gag atc      720
Asp Ser Asp Tyr Pro Leu Thr Phe Gly Gly Gly Thr Lys Leu Glu Ile
225                 230                 235                 240 aaa cgt                                                              726
Lys Arg <210> SEQ ID NO 4
<211> LENGTH: 242
<212> TYPE: PRT
<213> ORGANISM: Homo sapiens

<400> SEQUENCE: 4

Gly Arg Gly Ala Leu Val Glu Ser Gly Pro Gly Leu Val Lys Pro Ser
1               5                   10                  15

Glu Thr Leu Phe Leu Thr Cys Thr Val Ser Gly Gly Ser Ile Ser Ser
            20                  25                  30

Tyr Tyr Trp Ser Trp Ile Arg Gln Pro Ala Gly Lys Gly Leu Glu Trp
        35                  40                  45

Ile Ala Tyr Ile Tyr Tyr Ser Gly Ser Thr Asn Tyr Asn Pro Ser Leu
    50                  55                  60

Lys Ser Arg Val Thr Ile Ser Val Asp Thr Ser Asn Asn Gln Phe Ser
65                  70                  75                  80

Leu Lys Leu Ser Ser Val Thr Ala Ala Asp Thr Ala Val Tyr Tyr Cys
                85                  90                  95

Ala Lys Leu Thr Ala Ala Gly Gly His Phe Asp Pro Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Val Met Thr Gln Ser Pro Ser Ser
    130                 135                 140

Leu Ser Ala Ser Ile Gly Asp Arg Val Thr Ile Thr Cys Arg Ala Ser
145                 150                 155                 160

Gln Gly Ile Ser Asn Phe Leu Ala Trp Phe Gln Gln Lys Pro Gly Lys
                165                 170                 175

Ala Pro Lys Ser Leu Ile Tyr Ala Ala Ser Ser Leu Gln Ser Gly Val
            180                 185                 190
```

```
Pro Ser Lys Phe Ser Gly Ser Gly Ser Gly Thr Asp Phe Thr Leu Ala
        195                 200                 205

Ile Ser Ser Leu Gln Pro Glu Asp Phe Ala Thr Tyr Tyr Cys Leu Gln
    210                 215                 220

Asp Ser Asp Tyr Pro Leu Thr Phe Gly Gly Gly Thr Lys Leu Glu Ile
225                 230                 235                 240

Lys Arg

<210> SEQ ID NO 5
<211> LENGTH: 777
<212> TYPE: DNA
<213> ORGANISM: Pseudomonas aeruginosa
<220> FEATURE:
<221> NAME/KEY: CDS
<222> LOCATION: (1)..(777)

<400> SEQUENCE: 5 cgc cat cgt cag ccg cgt ggc tgg gaa cag ctg gca gac gtg gtt tcc        48
Arg His Arg Gln Pro Arg Gly Trp Glu Gln Leu Ala Asp Val Val Ser
1               5                   10                  15 ctg acc tgt ccg gtt gct gcg ggc gaa tgt gcg ggt ccg gca gat tcc        96
Leu Thr Cys Pro Val Ala Ala Gly Glu Cys Ala Gly Pro Ala Asp Ser
            20                  25                  30 ggt gat gca ctg ctg gaa cgt aac tat ccg acc ggc gcc gaa ttt ctg       144
Gly Asp Ala Leu Leu Glu Arg Asn Tyr Pro Thr Gly Ala Glu Phe Leu
        35                  40                  45 ggt gat ggc ggt gca att tca ttc tcg acc cgc ggc acg cag aat tgg       192
Gly Asp Gly Gly Ala Ile Ser Phe Ser Thr Arg Gly Thr Gln Asn Trp
    50                  55                  60 acg gtg gaa cgt ctg ctg caa gcc cat cgc caa ctg gaa gaa ggc ggt       240
Thr Val Glu Arg Leu Leu Gln Ala His Arg Gln Leu Glu Glu Gly Gly
65                  70                  75                  80 tat gtt ttt gtc ggc tat cat ggc acc ttt ctg gaa gcc gca cag tca       288
Tyr Val Phe Val Gly Tyr His Gly Thr Phe Leu Glu Ala Ala Gln Ser
                85                  90                  95 atc gtg ttt ggc ggt gtt cgt gcg cgc tcg cag gat ctg gat gct att       336
Ile Val Phe Gly Gly Val Arg Ala Arg Ser Gln Asp Leu Asp Ala Ile
            100                 105                 110 tgg gcg ggc ttc tac atc gcc ggt gat ccg gcg ctg gcg tat ggc tac       384
Trp Ala Gly Phe Tyr Ile Ala Gly Asp Pro Ala Leu Ala Tyr Gly Tyr
        115                 120                 125 gca cag gat caa gaa ccg gac gct gcg ggc cgt att cgc aac ggt gcg       432
Ala Gln Asp Gln Glu Pro Asp Ala Ala Gly Arg Ile Arg Asn Gly Ala
    130                 135                 140 ctg ctg cgt gtg tat gtt ccg cgc agc tct ctg ccg ggc ttt tat gca       480
Leu Leu Arg Val Tyr Val Pro Arg Ser Ser Leu Pro Gly Phe Tyr Ala
145                 150                 155                 160 acc ggt ctg acg ctg gcc gca ccg gaa gct gcg ggc gaa gtg gaa cgt       528
Thr Gly Leu Thr Leu Ala Ala Pro Glu Ala Ala Gly Glu Val Glu Arg
                165                 170                 175 ctg att ggt cac ccg ctg ccg ctg cgc ctg gat gct atc acc ggt ccg       576
Leu Ile Gly His Pro Leu Pro Leu Arg Leu Asp Ala Ile Thr Gly Pro
            180                 185                 190 gaa gaa gcg ggc ggt cgt ctg gaa acg att ctg ggt tgg ccg ctg gct       624
Glu Glu Ala Gly Gly Arg Leu Glu Thr Ile Leu Gly Trp Pro Leu Ala
        195                 200                 205 gaa cgc acc gtc gtg att ccg agc gcg atc ccg acc gat ccg cgt aat       672
Glu Arg Thr Val Val Ile Pro Ser Ala Ile Pro Thr Asp Pro Arg Asn
    210                 215                 220
```

```
gtt ggc ggt gat ctg gac ccg agt tcc atc ccg gac tct gaa gcc gca      720
Val Gly Gly Asp Leu Asp Pro Ser Ser Ile Pro Asp Ser Glu Ala Ala
225                 230                 235                 240 atc tca gcc ctg ccg gat tat gcc agc caa ccg ggt aaa ccg ccg aaa      768
Ile Ser Ala Leu Pro Asp Tyr Ala Ser Gln Pro Gly Lys Pro Pro Lys
                245                 250                 255 gac gaa ctg                                                          777
Asp Glu Leu
```

<210> SEQ ID NO 6
<211> LENGTH: 259
<212> TYPE: PRT
<213> ORGANISM: Pseudomonas aeruginosa

<400> SEQUENCE: 6

Arg His Arg Gln Pro Arg Gly Trp Glu Gln Leu Ala Asp Val Val Ser
1               5                   10                  15

Leu Thr Cys Pro Val Ala Ala Gly Glu Cys Ala Gly Pro Ala Asp Ser
            20                  25                  30

Gly Asp Ala Leu Leu Glu Arg Asn Tyr Pro Thr Gly Ala Glu Phe Leu
        35                  40                  45

Gly Asp Gly Gly Ala Ile Ser Phe Ser Thr Arg Gly Thr Gln Asn Trp
    50                  55                  60

Thr Val Glu Arg Leu Leu Gln Ala His Arg Gln Leu Glu Glu Gly Gly
65                  70                  75                  80

Tyr Val Phe Val Gly Tyr His Gly Thr Phe Leu Glu Ala Ala Gln Ser
                85                  90                  95

Ile Val Phe Gly Gly Val Arg Ala Arg Ser Gln Asp Leu Asp Ala Ile
            100                 105                 110

Trp Ala Gly Phe Tyr Ile Ala Gly Asp Pro Ala Leu Ala Tyr Gly Tyr
        115                 120                 125

Ala Gln Asp Gln Glu Pro Asp Ala Ala Gly Arg Ile Arg Asn Gly Ala
    130                 135                 140

Leu Leu Arg Val Tyr Val Pro Arg Ser Ser Leu Pro Gly Phe Tyr Ala
145                 150                 155                 160

Thr Gly Leu Thr Leu Ala Ala Pro Glu Ala Ala Gly Glu Val Glu Arg
                165                 170                 175

Leu Ile Gly His Pro Leu Pro Leu Arg Leu Asp Ala Ile Thr Gly Pro
            180                 185                 190

Glu Glu Ala Gly Gly Arg Leu Glu Thr Ile Leu Gly Trp Pro Leu Ala
        195                 200                 205

Glu Arg Thr Val Val Ile Pro Ser Ala Ile Pro Thr Asp Pro Arg Asn
    210                 215                 220

Val Gly Gly Asp Leu Asp Pro Ser Ser Ile Pro Asp Ser Glu Ala Ala
225                 230                 235                 240

Ile Ser Ala Leu Pro Asp Tyr Ala Ser Gln Pro Gly Lys Pro Pro Lys
                245                 250                 255

Asp Glu Leu

<210> SEQ ID NO 7
<211> LENGTH: 27
<212> TYPE: DNA
<213> ORGANISM: Artificial Sequence
<220> FEATURE:
<223> OTHER INFORMATION: Sequence of connector
<220> FEATURE:
<221> NAME/KEY: CDS
<222> LOCATION: (1)..(27)

<400> SEQUENCE: 7

```
gct agc ggc ggc ccg gaa ggc ggc agc                                    27
Ala Ser Gly Gly Pro Glu Gly Gly Ser
1               5
```

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

```
Ala Ser Gly Gly Pro Glu Gly Gly Ser
1               5
```

<210> SEQ ID NO 9
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 9

```
ggt cga ggt gca ctg gtg gag tct ggc cca gga ctg gtg aag cct tcg       48
Gly Arg Gly Ala Leu Val Glu Ser Gly Pro Gly Leu Val Lys Pro Ser
1               5                   10                  15 gag acc ctg ttc ctc acc tgc act gtc tct ggt ggc tcc atc agt tct       96
Glu Thr Leu Phe Leu Thr Cys Thr Val Ser Gly Gly Ser Ile Ser Ser
            20                  25                  30 tac tac tgg agc tgg atc cgg cag ccc gca ggg aag gga ctg gag tgg     144
Tyr Tyr Trp Ser Trp Ile Arg Gln Pro Ala Gly Lys Gly Leu Glu Trp
        35                  40                  45 att gcg tat atc tat tac agt ggg agc acc aac tac aac ccc tcc ctc     192
Ile Ala Tyr Ile Tyr Tyr Ser Gly Ser Thr Asn Tyr Asn Pro Ser Leu
    50                  55                  60 aag agt cga gtc acc ata tca gta gac acg tcc aac aac cag ttc tcc     240
Lys Ser Arg Val Thr Ile Ser Val Asp Thr Ser Asn Asn Gln Phe Ser
65                  70                  75                  80 ctg aaa ctg agc tct gtg acc gct gcg gac acg gcc gtg tat tat tgt     288
Leu Lys Leu Ser Ser Val Thr Ala Ala Asp Thr Ala Val Tyr Tyr Cys
                85                  90                  95 gcg aag tta aca gca gcc ggg ggc cac ttc gac ccc tgg ggc cag ggc     336
Ala Lys Leu Thr Ala Ala Gly Gly His Phe Asp Pro Trp Gly Gln Gly
            100                 105                 110 acc ctg gtc acc gtc tcc tca                                          357
Thr Leu Val Thr Val Ser Ser
        115
```

<210> SEQ ID NO 10
<211> LENGTH: 119
<212> TYPE: PRT
<213> ORGANISM: Homo sapiens

<400> SEQUENCE: 10

```
Gly Arg Gly Ala Leu Val Glu Ser Gly Pro Gly Leu Val Lys Pro Ser
1               5                   10                  15

Glu Thr Leu Phe Leu Thr Cys Thr Val Ser Gly Gly Ser Ile Ser Ser
            20                  25                  30

Tyr Tyr Trp Ser Trp Ile Arg Gln Pro Ala Gly Lys Gly Leu Glu Trp
        35                  40                  45
```

Ile Ala Tyr Ile Tyr Tyr Ser Gly Ser Thr Asn Tyr Asn Pro Ser Leu
        50                  55                  60

Lys Ser Arg Val Thr Ile Ser Val Asp Thr Ser Asn Asn Gln Phe Ser
65                  70                  75                  80

Leu Lys Leu Ser Ser Val Thr Ala Ala Asp Thr Ala Val Tyr Tyr Cys
                85                  90                  95

Ala Lys Leu Thr Ala Ala Gly Gly His Phe Asp Pro Trp Gly Gln Gly
            100                 105                 110

Thr Leu Val Thr Val Ser Ser
        115

<210> SEQ ID NO 11
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 11 gac atc gtg atg acc cag tct cca tcc tcc ctg tct gca tct ata ggg      48
Asp Ile Val Met Thr Gln Ser Pro Ser Ser Leu Ser Ala Ser Ile Gly
1               5                   10                  15 gac aga gtc acc atc act tgt cgg gca agt cag ggc att agc aat ttt      96
Asp Arg Val Thr Ile Thr Cys Arg Ala Ser Gln Gly Ile Ser Asn Phe
            20                  25                  30 tta gcc tgg ttt cag cag aaa cca ggg aaa gcc cct aag tcc ctg atc     144
Leu Ala Trp Phe Gln Gln Lys Pro Gly Lys Ala Pro Lys Ser Leu Ile
        35                  40                  45 tat gct gca tcc agt ttg caa agt ggg gtc cca tca aag ttc agc ggc     192
Tyr Ala Ala Ser Ser Leu Gln Ser Gly Val Pro Ser Lys Phe Ser Gly
    50                  55                  60 agt gga tct ggg aca gat ttc act ctc gcc atc agc agc ctg cag cct     240
Ser Gly Ser Gly Thr Asp Phe Thr Leu Ala Ile Ser Ser Leu Gln Pro
65                  70                  75                  80 gaa gat ttt gca act tat tac tgt ctc caa gat tcc gat tat cct ctc     288
Glu Asp Phe Ala Thr Tyr Tyr Cys Leu Gln Asp Ser Asp Tyr Pro Leu
                85                  90                  95 act ttc ggc gga ggg acc aag ctg gag atc aaa cgt                     324
Thr Phe Gly Gly Gly Thr Lys Leu Glu Ile Lys Arg
            100                 105

<210> SEQ ID NO 12
<211> LENGTH: 108
<212> TYPE: PRT
<213> ORGANISM: Homo sapiens

<400> SEQUENCE: 12

Asp Ile Val Met Thr Gln Ser Pro Ser Ser Leu Ser Ala Ser Ile Gly
1               5                   10                  15

Asp Arg Val Thr Ile Thr Cys Arg Ala Ser Gln Gly Ile Ser Asn Phe
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Ala Ile Ser Ser Leu Gln Pro
65                  70                  75                  80

Glu Asp Phe Ala Thr Tyr Tyr Cys Leu Gln Asp Ser Asp Tyr Pro Leu

Thr Phe Gly Gly Gly Thr Lys Leu Glu Ile Lys Arg
        100                 105

<210> SEQ ID NO 13
<211> LENGTH: 45
<212> TYPE: DNA
<213> ORGANISM: Artificial Sequence
<220> FEATURE:
<223> OTHER INFORMATION: Sequence of linker
<220> FEATURE:
<221> NAME/KEY: CDS
<222> LOCATION: (1)..(45)

<400> SEQUENCE: 13

```
ggt gga ggc ggt tca ggc gga ggt ggc agc ggc ggt ggc gga tcg       45
Gly Gly Gly Gly Ser Gly Gly Gly Gly Ser Gly Gly Gly Gly Ser
1               5                   10                  15
```

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 5
<212> TYPE: PRT
<213> ORGANISM: Artificial Sequence
<220> FEATURE:
<223> OTHER INFORMATION: Sequence of CDR1 of VH

<400> SEQUENCE: 15

Ser Tyr Tyr Trp Ser
1               5

<210> SEQ ID NO 16
<211> LENGTH: 16
<212> TYPE: PRT
<213> ORGANISM: Artificial Sequence
<220> FEATURE:
<223> OTHER INFORMATION: Sequence of CDR2 of VH

<400> SEQUENCE: 16

Tyr Ile Tyr Tyr Ser Gly Ser Thr Asn Tyr Asn Pro Ser Leu Lys Ser
1               5                   10                  15

<210> SEQ ID NO 17
<211> LENGTH: 10
<212> TYPE: PRT
<213> ORGANISM: Artificial Sequence
<220> FEATURE:
<223> OTHER INFORMATION: Sequence of CDR3 of VH

<400> SEQUENCE: 17

Leu Thr Ala Ala Gly Gly His Phe Asp Pro
1               5                   10

<210> SEQ ID NO 18
<211> LENGTH: 11
<212> TYPE: PRT
<213> ORGANISM: Artificial Sequence

```
<220> FEATURE:
<223> OTHER INFORMATION: Sequence of CDR1 of VL

<400> SEQUENCE: 18

Arg Ala Ser Gln Gly Ile Ser Asn Phe Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Sequence of CDR2 of VL

<400> SEQUENCE: 19

Ala Ala Ser Ser Leu Gln Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Sequence of CDR3 of VL

<400> SEQUENCE: 20

Leu Gln Asp Ser Asp Tyr Pro Leu Thr
1               5

<210> SEQ ID NO 21
<211> LENGTH: 11
<212> TYPE: PRT
<213> ORGANISM: Artificial Sequence
<220> FEATURE:
<223> OTHER INFORMATION: Sequence of furin cleavage site of PEA

<400> SEQUENCE: 21

Arg His Arg Gln Pro Arg Gly Trp Glu Gln Leu
1               5                   10

<210> SEQ ID NO 22
<211> LENGTH: 40
<212> TYPE: PRT
<213> ORGANISM: Artificial Sequence
<220> FEATURE:
<223> OTHER INFORMATION: Sequence of domain Ib of PEA

<400> SEQUENCE: 22

Ala Asp Val Val Ser Leu Thr Cys Pro Val Ala Ala Gly Glu Cys Ala
1               5                   10                  15

Gly Pro Ala Asp Ser Gly Asp Ala Leu Leu Glu Arg Asn Tyr Pro Thr
            20                  25                  30

Gly Ala Glu Phe Leu Gly Asp Gly
            35                  40

<210> SEQ ID NO 23
<211> LENGTH: 204
<212> TYPE: PRT
<213> ORGANISM: Artificial Sequence
<220> FEATURE:
<223> OTHER INFORMATION: Sequence domain III of PEA

<400> SEQUENCE: 23

Gly Ala Ile Ser Phe Ser Thr Arg Gly Thr Gln Asn Trp Thr Val Glu
1               5                   10                  15
```

```
Arg Leu Leu Gln Ala His Arg Gln Leu Glu Glu Gly Tyr Val Phe
            20                  25                  30

Val Gly Tyr His Gly Thr Phe Leu Glu Ala Ala Gln Ser Ile Val Phe
            35                  40                  45

Gly Gly Val Arg Ala Arg Ser Gln Asp Leu Asp Ala Ile Trp Ala Gly
        50                  55                  60

Phe Tyr Ile Ala Gly Asp Pro Ala Leu Ala Tyr Gly Tyr Ala Gln Asp
 65              70                  75                  80

Gln Glu Pro Asp Ala Ala Gly Arg Ile Arg Asn Gly Ala Leu Leu Arg
                85                  90                  95

Val Tyr Val Pro Arg Ser Ser Leu Pro Gly Phe Tyr Ala Thr Gly Leu
            100                 105                 110

Thr Leu Ala Ala Pro Glu Ala Ala Gly Glu Val Glu Arg Leu Ile Gly
            115                 120                 125

His Pro Leu Pro Leu Arg Leu Asp Ala Ile Thr Gly Pro Glu Glu Ala
            130                 135                 140

Gly Gly Arg Leu Glu Thr Ile Leu Gly Trp Pro Leu Ala Glu Arg Thr
145                 150                 155                 160

Val Val Ile Pro Ser Ala Ile Pro Thr Asp Pro Arg Asn Val Gly Gly
            165                 170                 175

Asp Leu Asp Pro Ser Ser Ile Pro Asp Ser Glu Ala Ala Ile Ser Ala
            180                 185                 190

Leu Pro Asp Tyr Ala Ser Gln Pro Gly Lys Pro Pro
            195                 200

<210> SEQ ID NO 24
<211> LENGTH: 4
<212> TYPE: PRT
<213> ORGANISM: Artificial Sequence
<220> FEATURE:
<223> OTHER INFORMATION: Sequence of carboxy terminal of PEA

<400> SEQUENCE: 24

Lys Asp Glu Leu
1

<210> SEQ ID NO 25
<211> LENGTH: 10
<212> TYPE: PRT
<213> ORGANISM: Homo sapiens

<400> SEQUENCE: 25

Ser Glu Gln Asp Gln Asp Pro Gln Arg Val
1               5                   10
```